US011359213B2

(12) United States Patent
Wang

(10) Patent No.: US 11,359,213 B2
(45) Date of Patent: *Jun. 14, 2022

(54) METHODS FOR ANALYSIS OF VIRAL CAPSID PROTEIN COMPOSITION

(71) Applicant: Regeneron Pharmaceuticals, Inc., Tarrytown, NY (US)

(72) Inventor: Shunhai Wang, Scarsdale, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/897,617

(22) Filed: Jun. 10, 2020

(65) Prior Publication Data

US 2020/0299728 A1 Sep. 24, 2020

Related U.S. Application Data

(63) Continuation-in-part of application No. 16/663,109, filed on Oct. 24, 2019.

(60) Provisional application No. 62/750,583, filed on Oct. 25, 2018.

(51) Int. Cl.
*C12N 15/86* (2006.01)
*C12N 7/00* (2006.01)
*G01N 30/02* (2006.01)
*C07K 1/20* (2006.01)
*G01N 30/06* (2006.01)

(52) U.S. Cl.
CPC ............. *C12N 15/86* (2013.01); *C12N 7/00* (2013.01); *G01N 30/02* (2013.01); *C07K 1/20* (2013.01); *C12N 2710/14143* (2013.01); *C12N 2750/14142* (2013.01); *C12N 2750/14143* (2013.01); *C12N 2750/14152* (2013.01); *G01N 2030/027* (2013.01); *G01N 2030/062* (2013.01)

(58) Field of Classification Search
CPC ...................... C12N 15/86; C12N 7/00; C12N 2710/14143; C12N 2750/14142; C12N 2750/14143; C12N 2750/14152; G01N 30/02; G01N 2030/027; G01N 2030/062; G01N 33/6848; G01N 33/6803; G01N 30/7233; C07K 1/20; C07K 16/2896; C12Y 302/0102

See application file for complete search history.

(56) References Cited

U.S. PATENT DOCUMENTS 8,946,395 B1 * 2/2015 Herigstad ................ C07K 1/20
530/412

FOREIGN PATENT DOCUMENTS

WO 2018/035059 A1 2/2018

OTHER PUBLICATIONS

Aloor A, Zhang J, Gashash EA, Parameswaran A, Chrzanowski M, Ma C, Diao Y, Wang PG, Xiao W. Site-Specific N-Glycosylation on the AAV8 Capsid Protein. Viruses. Nov. 17, 2018;10(11):644. (Year: 2018).*
Gargano AFG, Roca LS, Fellers RT, Bocxe M, Dominguez-Vega E, Somsen GW. Capillary HILIC-MS: A New Tool for Sensitive Top-Down Proteomics. Anal Chem. Jun. 5, 2018;90(11):6601-6609. Epub May 18, 2018. (Year: 2018).*
Jin X, Liu L, Nass S, O'Riordan C, Pastor E, Zhang XK. Direct Liquid Chromatography/Mass Spectrometry Analysis for Complete Characterization of Recombinant Adeno-Associated Virus Capsid Proteins. Hum Gene Ther Methods. Oct. 2017;28(5):255-267. Epub Jun. 16, 2017. (Year: 2017).*
Liu AP, Patel SK, Xing T, Yan Y, Wang S, Li N. Characterization of Adeno-Associated Virus Capsid Proteins Using Hydrophilic Interaction Chromatography Coupled with Mass Spectrometry. J Pharm Biomed Anal. Sep. 10, 2020;189:113481. Epub Jul. 21, 2020. (Year: 2020).*
Yang X, Bartlett MG. Glycan analysis for protein therapeutics. J Chromatogr B Analyt Technol Biomed Life Sci. Jul. 1, 2019;1120:29-40. Epub Apr. 26, 2019. (Year: 2019).*
Pritchard LK, Vasiljevic S, Ozorowski G, Seabright GE, Cupo A, Ringe R, Kim HJ, Sanders RW, Doores KJ, Burton DR, Wilson IA, Ward AB, Moore JP, Crispin M. Structural Constraints Determine the Glycosylation of HIV-1 Envelope Trimers. Cell Rep. Jun. 16, 2015;11(10):1604-13. Epub Jul. 4, 2015. (Year: 2015).*
Wang S, Liu AP, Yan Y, Daly TJ, Li N. Characterization of product-related low molecular weight impurities in therapeutic monoclonal antibodies using hydrophilic interaction chromatography coupled with mass spectrometry. J Pharm Biomed Anal. May 30, 2018;154:468-475. Epub Mar. 16, 2018. (Year: 2018).
Michen B, Graule T. Isoelectric points of viruses. J Appl Microbiol. Aug. 2010;109(2):388-97. Epub Jan. 22, 2010. (Year 2010).
Potter M, Lins B, Mietzsch M, Heilbronn R, Van Vliet K, Chipman P, Agbandje-McKenna M, Cleaver BD, Clement N, Byrne BJ, Zolotukhin S. A simplified purification protocol for recombinant adeno-associated virus vectors. Mol Ther Methods Clin Dev. Aug. 13, 2014;1:14034. (Year: 2014).
P. Gagnon, E. Grund, T. Lindback. Large-scale process development for hydrophobic interaction chromatography, part 2: controlling process variation. Biopharm, 8 (1995), pp. 36-41. (Year: 1995).

(Continued)

Primary Examiner — Rachel B Gill
(74) Attorney, Agent, or Firm — Kramer Levin Naftalis & Frankel LLP

(57) ABSTRACT

Methods of determining the stoichiometry of a viral capsid and/or determining the heterogeneity of protein components in a viral capsid are disclosed.

22 Claims, 15 Drawing Sheets

(56) References Cited

OTHER PUBLICATIONS

P. Gagnon, E. Grund, T. Lindback. Large scale process development for hydrophobic interaction chromatography, part 1: gel selection and development of binding conditions. Biopharm, 8 (1995), pp. 21-27. (Year: 1995).

Weigel T, Soliman R, Wolff MW, Reichl U. Hydrophobic-interaction chromatography for purification of influenza A and B virus. J Chromatogr B Analyt Technol Biomed Life Sci. Jun. 1, 2019;1117:103-117. Epub Apr. 1, 2019. (Year: 2019).

Wolff MW, Siewert C, Hansen SP, Faber R, Reichl U. Purification of cell culture-derived modified vaccinia ankara virus by pseudo-affinity membrane adsorbers and hydrophobic interaction chromatography. Biotechnol Bioeng. Oct. 1, 2010;107(2):312-20. (Year: 2010).

Li H, Yang Y, Zhang Y, Zhang S, Zhao Q, Zhu Y, Zou X, Yu M, Ma G, Su Z. A hydrophobic interaction chromatography strategy for purification of inactivated foot-and-mouth disease virus. Protein Expr Purif. Sep. 2015;113:23-9. Epub May 6, 2015. (Year: 2015).

Shytuhina Anastasija et al., "Development and application of a reversed-phase high-performance liquid chromatographic method for quantitation and characterization of a Chikungunya virus-like particle vaccine," Journal of Chromatography A., Elsevier Amsterdam, NL, vol. 1364, Jun. 19, 2014, pp. 192-197.

Marco Benevento et al.: "Adenovirus Composition, Proteolysis, and Disassembly Studied by in-depth Qualitative and Quantitative Proteomics," Journal of Biological Chemistry, vol. 289, No. 16, Mar. 3, 2014, pp. 11421-11430.

International Search Report PCT Application No. PCT/US2019/057936, International Filing Date Oct. 24, 2019, dated Jan. 31, 2020.

Sviben D, Forcic D, et al. Recovery of infective virus particles in ion-exchange and hydrophobic interaction monolith chromatography is influenced by particle charge and total-to-infective particle ration. J Chromatogr. B. Analyt. Technol. Biomed. Life Science Jun. 1, 2017;1054:10-19. Epub Apr. 8, 2017 (2017).

* cited by examiner

VP1    VP2    VP3
34 46 118 139 161 261 266 328 381 447 449 459 522 534 553 573 584 587 588 591 664

M.W. of VP1 ~ 81.5 kDa
M.W. of VP2 ~ 66.4 kDa
M.W. of VP3 ~ 59.9 kDa

FIG. 8B
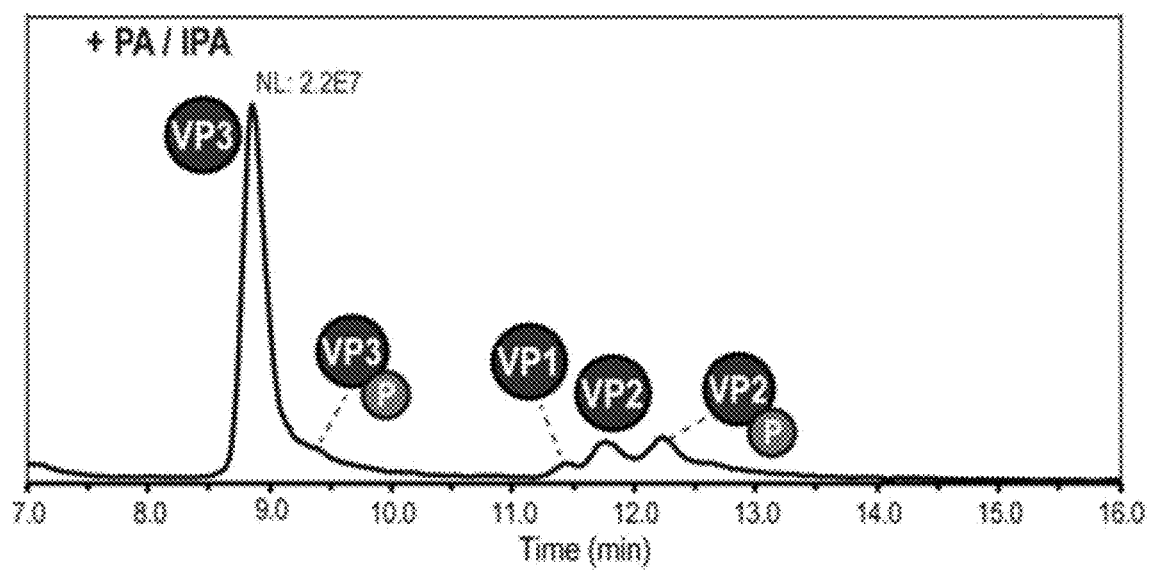
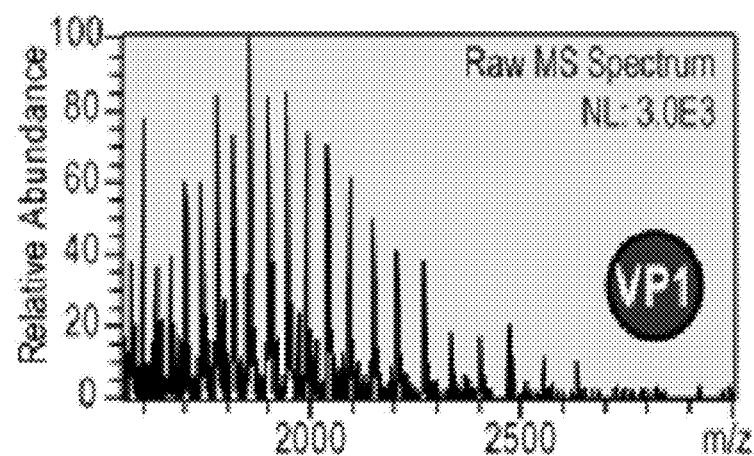

METHODS FOR ANALYSIS OF VIRAL CAPSID PROTEIN COMPOSITION

CROSS-REFERENCE TO RELATED APPLICATIONS

This application is a continuation-in-part of U.S. patent application Ser. No. 16/663,109, filed on Oct. 24, 2019, which claims the benefit of U.S. Provisional Patent Application No. 62/750,583, filed on Oct. 25, 2018. The contents of each of these applications are incorporated by reference in their entirety.

FIELD OF THE INVENTION

The present invention pertains to methods for determining the heterogeneity of a viral particle, such as an adeno-associated virus (AAV) particle using hydrophilic interaction liquid chromatography (HILIC) and mass spectrometry determination.

BACKGROUND

Gene therapy has emerged as an alternative treatment for genetic diseases. Gene therapy involves the transfer of some genetic material (DNA, RNA or oligonucleotides) into target cells. In practice, the gene of interest (also called a transgene) must be delivered to the cell by a vector, which carries a molecule of DNA or RNA. It is based on the transfer of functional genes to replace or supplement defective genes. The transgene can be delivered into the cell by the vector. The method of delivery differs depending on the type of treatment and organ/tissue to be targeted.

Viral particles have emerged as vectors for gene therapy and the treatment of disease. Viral vectors, such as those based on the genome of adeno-associated virus (AAV), offer exciting platforms for gene delivery. Currently, 12 human serotypes of AAV (AAV1-12) have been described, many of which have distinct cell and tissue tropism, potentially creating the option to generate a variety of different vector classes from this viral genus.

However, one of the problems facing the adoption of viral vectors in gene therapy is the characterization of viral particle homogeneity. While classic techniques such as electron microscopy and Southern Blots can characterize viral particle heterogeneity, such as AAV heterogeneity and aggregation, they do not provide sufficient resolution for quantifying homogeneity when it comes to producing clinical-grade viral vector preparations. Complete characterization of the constituent viral capsid proteins, such as the capsid proteins of AAV vectors, including their sequences and post-translational modifications (PTMs), is highly recommended to ensure product quality and consistency. Thus, methods are needed to determine the homogeneity of viral particles.

SUMMARY OF THE INVENTION

In one aspect, the present invention provides a method of determining the stoichiometry of protein components of a viral capsid of a viral particle, in which the method comprises: (a) subjecting a sample of viral particles to hydrophilic interaction liquid chromatography (HILIC) to separate the protein components of the viral capsid of the viral particles; (b) determining the masses of protein components of the viral capsid to identify the protein components separated by HILIC; and (c) determining the relative abundance of the protein components of the viral capsid from the HILIC separation, thereby determining the stoichiometry of protein components of a viral capsid of a viral particle.

In another aspect, the present invention provides a method of determining the heterogeneity of proteins in a capsid of a viral particle, in which the method comprises: (a) subjecting the viral particle to HILIC to separate protein components of the viral particle capsid; (b) determining the masses of protein components of the protein capsid; and (c) comparing the determined masses of the protein components of the viral particle capsid with theoretical masses, wherein a deviation of one or more of the masses of protein components of the viral particle capsid from the theoretical masses is indicative of the capsid heterogeneity.

In some embodiments, the viral particle comprises an adeno-associated virus (AAV) particle.

In some embodiments, the protein components of the viral capsid comprise VP1, VP2 and VP3 of the AAV particle.

In some embodiments, the heterogeneity comprises one or more of mixed serotypes, variant capsids, capsid amino acid substitutions, truncated capsids, or modified capsids.

In some aspects, the AAV particle comprises an AAV1 capsid, an AAV2 capsid, an AAV3 capsid, an AAV4 capsid, an AAV5 capsid, an AAV6 capsid, an AAV7 capsid, an AAV8 capsid, an AAVrh8 capsid, an AAV9 capsid, an AAV10 capsid, an AAV11 capsid, an AAV 12 capsid, or a variant thereof.

In some embodiments, the masses of VP1, VP2, and VP3 are compared to theoretical masses of one or more of an AAV1 capsid, an AAV2 capsid, an AAV3 capsid, an AAV4 capsid, an AAV5 capsid, an AAV6 capsid, an AAV7 capsid, an AAV8 capsid, AAVrh8 capsid, an AAV9 capsid, an AAV10 capsid, an AAV11 capsid, an AAV 12 capsid, or a variant thereof.

In some aspects, the AAV particle comprises an AAV1 inverted terminal repeat sequence (ITR), an AAV2 ITR, an AAV3 ITR, an AAV4 ITR, an AAV5 ITR, an AAV6 ITR, an AAV7 ITR, an AAV8 ITR, an AAVrh8 ITR, an AAV9 ITR, an AAV 10 ITR, an AAVrh10 ITR, an AAV11 ITR, or an AAV 12 ITR.

In some aspects, the AAV particle has a capsid serotype selected for transduction of cells of a subject's liver.

In some aspects, the AAV particle is a recombinant AAV (rAAV) particle.

In some aspects, the AAV particle comprises an AAV vector encoding a heterologous transgene.

In other aspects, the AAV particle has a capsid serotype AAV7, AAV8, or AAV9.

In other aspects, the AAV particle has a capsid serotype AAV9.

In other aspects, the AAV particle has a capsid serotype AAV9 and is a viral vector encoding Lysosomal Alpha Glucosidase (GAA) linked to an anti-CD63 antibody.

In some aspects, the viral particle comprises a viral vector encoding a heterologous transgene.

In some aspects, the viral particle belongs to a viral family selected from the group consisting of Adenoviridae, Parvoviridae, Retroviridae, Baculoviridae, and Herpesviridae.

In some aspects, the viral particle belongs to a viral genus selected from the group consisting of Atadenovirus, Aviadenovirus, Ichtadenovirus, Mastadenovirus, Siadenovirus, Ambidensovirus, Brevidensovirus, Hepandensovirus, Iteradensovirus, Penstyldensovirus, Amdoparvovirus, Aveparvovirus, Bocaparvovirus, Copiparvovirus, Dependoparvovirus, Erythroparvovirus, Protoparvovirus, Tetraparvovirus, Alpharetrovirus, Betaretrovirus, Deltaretrovirus, Epsilonretrovirus, Gammaretrovirus, Lentivirus, Spumavirus, Alphabaculovirus, Betabaculovirus, Deltabaculovirus, Gammabaculovirus, Iltovirus, Mardivirus, Simplexvirus, Varicellovirus, Cytomegalovirus, Muromegalovirus, Proboscivirus, Roseolovirus, Lymphocryptovirus, Macavirus, Percavirus, and Rhadinovirus.

In other aspects, the Retroviridae is Moloney murine sarcoma virus (MoMSV), Harvey murine sarcoma virus (HaMuSV), murine mammary tumor virus (MuMTV), gibbon ape leukemia virus (GaLV), feline leukemia virus (FLV), Spumavirus, Friend virus, Murine Stem Cell Virus (MSCV) Rous Sarcoma Virus (RSV), human T cell leukemia viruses, Human Immunodeficiency Virus (HIV), feline immunodeficiency virus (FIV), equine immunodeficiency virus (EIV), visna-maedi virus; caprine arthritis-encephalitis virus; equine infectious anemia virus; feline immunodeficiency virus (FIV); bovine immune deficiency virus (BIV); or simian immunodeficiency virus (SIV).

In some embodiments, the HILIC uses a mobile phase A comprising trifluoroacetic acid in water.

In some aspects, the mobile phase A comprises about 0.1% trifluoroacetic acid.

In some aspects, the chromatography comprises a mobile phase B comprising trifluoroacetic acid in acetonitrile.

In some aspects, the mobile phase B comprises about 0.1% trifluoroacetic acid.

In some aspects, the proportion of mobile phase A in the chromatography increases over time.

In some aspects, the mobile phase A increases from about 15% to about 100%, over about 45 minutes.

This disclosure, at least in part, provides a method for characterizing protein components of a viral capsid of a viral particle, comprising: subjecting a sample of the viral particles to hydrophilic interaction liquid chromatography (HILIC) to separate the protein components of the viral capsid of the viral particles, wherein the protein components are monitored using a fluorescence detector; and determining masses of the protein components of the viral capsid to identify the protein components separated by HILIC. In one aspect, a mobile phase of the HILIC comprises trifluoroacetic acid, wherein a desolvation gas is incorporated to the separation of the protein components. In one aspect, the desolvation gas comprises propionic acid and isopropanol, wherein a ratio of the propionic acid and the isopropanol is 3:1.

In one aspect, the sample of the viral particle is mixed with a liquid prior to loading to the HILIC, wherein the liquid comprises one or more components of a mobile phase of the HILIC. In one aspect, the sample of the viral particle is loaded to the HILIC by multiple injections, wherein the HILIC includes a wide-pore amide-bonded column. In one aspect, the method of the present application further comprises determining the relative abundance of the protein components based on the HILIC separation, thereby determining the stoichiometry of protein components of a viral capsid of a viral particle.

In another aspect, the method of the present application further comprises comparing the determined masses of the protein components with theoretical masses, wherein a deviation of one or more of the masses of protein components from the theoretical masses is indicative of capsid heterogeneity, wherein the capsid heterogeneity comprises one or more of mixed serotypes, variant capsids, capsid amino acid substitutions, truncated capsids, or modified capsids. In one aspect, the capsid heterogeneity is phosphorylation, oxidation or protein backbone clippings of the protein component.

In yet another aspect, the protein component is VP1, VP2 or VP3, wherein the viral particle is an adeno-associated virus (AAV) particle, and wherein a serotype of the AAV particle is AAV1, AAV2, AAV6, AAV7, AAV8, AAV9, AAVDJ, AAVhu37, or a variant thereof. In one aspect, the AAV particle comprises an AAV vector encoding a heterologous transgene.

DESCRIPTION OF THE FIGURES

FIG. 8B shows TICs of HILIC-FLR-MS analysis of AAV7 with desolvation gas (3:1 (v/v) mixture of propionic acid (PA) and isopropanol (IPA)) according to an exemplary embodiment.

DETAILED DESCRIPTION OF THE INVENTION

Before the present invention is further described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims. Any embodiments or features of embodiments can be combined with one another, and such combinations are expressly encompassed within the scope of the present invention.

Unless explained otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than about 1%. For example, as used herein, the expression "about 100" includes 99 and 101 and all values in between (e.g., 99.1, 99.2, 99.3, 99.4, etc.)

Although any methods and materials similar or equivalent to those described herein can be used in the practice or testing of the present invention, the preferred methods and materials are now described. All patents, applications and non-patent publications mentioned in this specification are incorporated herein by reference in their entireties.

Abbreviations Used Herein
  MS/MS: Tandem Mass Spectrometry
  MS: Mass Spectrometry
  ITRs: Inverted Terminal Repeat Sequences
  rAAV vector: Recombinant AAV Vector
  HILIC: Hydrophilic Interaction Liquid Chromatography
  GAA: Lysosomal Alpha Glucosidase
  mAb: Monoclonal Antibody
  IgG: Immunoglobulin G
  LC: Light Chain
  HC: Heavy Chain
  AAV: Adeno-Associated Virus
  PTMs: Post-translational Modifications
  ERT: enzyme replacement therapy "Adeno-associated virus" or "AAV": AAV is a non-pathogenic parvovirus, with single-stranded DNA, a genome of approximately 4.7 kb, not enveloped and has icosahedric conformation. AAV was first discovered in 1965 as a contaminant of adenovirus preparations. AAV belongs to the Dependovirus genus and Parvoviridae family, requiring helper functions from either herpes virus or adenovirus for replication. In the absence of helper virus, AAV can set up latency by integrating into human chromosome 19 at the 19q13.4 location. The AAV genome consists of two open reading frames (ORF), one for each of two AAV genes, Rep and Cap. The AAV DNA ends have a 145-bp inverted terminal repeat (ITR), and the 125 terminal bases are palindromic, leading to a characteristic T-shaped hairpin structure.

Figures 2A, 2B:
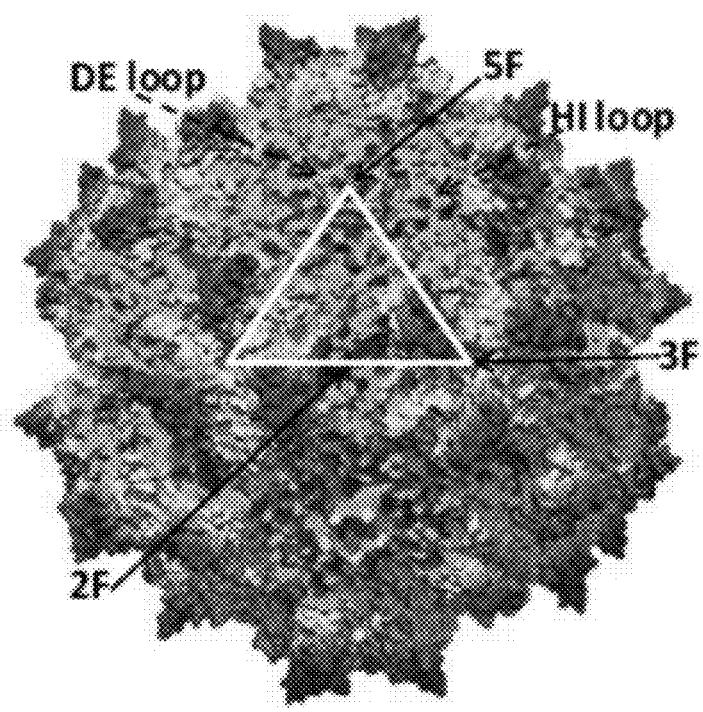
FIG. 2A is a model of an AAV viral capsid.
FIG. 2B is schematic representation of the viral capsid proteins from an AAV serotype and their approximate masses.

The Rep gene is transcribed from promoters p5 and p19 into four Rep proteins (Rep78, Rep68, Rep52, and Rep40), which have important roles in the life cycle of the virus. Proteins Rep78 and Rep68 are encoded by the mRNA transcribed from promoter p5. These proteins are essential for viral DNA replication, transcription and control of site-specific integration. The two smaller proteins Rep52 and Rep40 are generated by the mRNA transcribed from promoter p19. These proteins are involved in the formation of a single-stranded viral genome for packaging and viral integration. The Cap gene encodes three viral capsid proteins: VP1 (735 amino acids, ~90 kDa), VP2 (598 amino acids, ~72 kDa) and VP3 (533 amino acids, ~60 kDa), which form the viral capsid of 60 subunits, at the ratio of 1:1:10 (see FIGS. 2A and 2B). The three capsid proteins are translated from the mRNA transcribed from the promoter p40.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVD" or "$V_H$") and a heavy chain constant region (comprised of domains $C_H1$, $C_H2$ and $C_H3$). In various embodiments, the heavy chain may be an IgG isotype. In some cases, the heavy chain is selected from IgG1, IgG2, IgG3 or IgG4. In some embodiments, the heavy chain is of isotype IgG1 or IgG4, optionally including a chimeric hinge region of isotype IgG1/IgG2 or IgG4/IgG2. Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" includes antibody molecules prepared, expressed, created or isolated by recombinant means, such as antibodies isolated from a host cell transfected to express the antibody. For a review on antibody structure, see Lefranc et al., *IMGT unique numbering for immunoglobulin and T cell receptor variable domains and Ig superfamily V-like domains,* 27(1) Dev. Comp. Immunol. 55-77 (2003); and M. Potter, *Structural correlates of immunoglobulin diversity,* 2(1) Surv. Immunol. Res. 27-42 (1983).

The term antibody also encompasses a "bispecific antibody", which includes a heterotetrameric immunoglobulin that can bind to more than one different epitope. One half of the bispecific antibody, which includes a single heavy chain and a single light chain and six CDRs, binds to one antigen or epitope, and the other half of the antibody binds to a different antigen or epitope. In some cases, the bispecific antibody can bind the same antigen, but at different epitopes or non-overlapping epitopes. In some cases, both halves of the bispecific antibody have identical light chains while retaining dual specificity. Bispecific antibodies are described generally in U.S. Patent App. Pub. No. 2010/0331527 (Dec. 30, 2010).

The terms "antigen-binding portion" and "antigen-binding fragment" of an antibody (or "antibody fragment"), refers to one or more fragments of an antibody that retain the ability to specifically bind to an antigen. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 241:544-546), which consists of a VH domain, (vi) an isolated CDR, and (vii) an scFv, which consists of the two domains of the Fv fragment, VL and VH, joined by a synthetic linker to form a single protein chain in which the VL and VH regions pair to form monovalent molecules. Other forms of single chain antibodies, such as diabodies are also encompassed under the term "antibody" (see e.g., Holliger et at. (1993) 90 PNAS U.S.A. 6444-6448; and Poljak et at. (1994) 2 Structure 1121-1123).

Moreover, antibodies and antigen-binding fragments thereof can be obtained using standard recombinant DNA techniques commonly known in the art (see Sambrook et al., 1989).

The term "human antibody", is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

The term "corresponding" is a relative term indicating similarity in position, purpose or structure. A mass spectral signal due to a particular peptide or protein is also referred to as a signal corresponding to the peptide or protein. In certain embodiments, a particular peptide sequence or set of amino acids, such as a protein, can be assigned to a corresponding peptide mass.

The term "isolated," as used herein, refers to a biological component (such as a nucleic acid, peptide, protein, lipid, viral particle or metabolite) that has been substantially separated, produced apart from, or purified away from other biological components in the cell of the organism in which the component naturally occurs or is transgenically expressed.

"Mass spectrometry" is a method wherein, a sample is analyzed by generating gas phase ions from the sample, which are then separated according to their mass-to-charge ratio (m/z) and detected. Methods of generating gas phase ions from a sample include electrospray ionization (ESI), matrix-assisted laser desorption-ionization (MALDI), surface-enhanced laser desorption-ionization (SELDI), chemical ionization, and electron-impact ionization (EI). Separation of ions according to their m/z ratio can be accomplished with any type of mass analyzer, including quadrupole mass analyzers (Q), time-of-flight (TOF) mass analyzers, magnetic sector mass analyzers, 3D and linear ion traps (IT), orbitrap mass analyzer, Fourier-transform ion cyclotron resonance (FT-ICR) analyzers, and combinations thereof (for example, a quadrupole-time-of-flight analyzer, or Q-TOF analyzer). Prior to separation, the sample may be subjected to one or more dimensions of chromatographic separation, for example HILIC.

Tandem mass spectrometry or MS/MS is a technique to break down selected ions (precursor ions) into fragments (product ions). The fragments then reveal aspects of the chemical structure of the precursor ion. In tandem mass spectrometry, once samples are ionized (for example by ESI, MALDI, EI, etc.) to generate a mixture of ions, precursor ions, for example peptides from a digest, of a specific mass-to-charge ratio (m/z) are selected (MS1) and then fragmented (MS2) to generate a product ions for detection. Typical Tandem MS instruments include QqQ, QTOF, and hybrid ion trap/FTMS, etc. One example of an application of tandem mass spectrometry is protein identification. The first mass analyzer isolates ions of a particular m/z value that represent a single species of peptide among many introduced into and then emerging from the ion source. Those ions are then accelerated into a collision cell containing an inert gas such as argon to induce ion fragmentation. This process is designated collisionally induced dissociation (CID) or collisionally activated dissociation (CAD). The m/z values of fragment ions are then measured in a $2^{nd}$ mass analyzer to obtain amino acid sequence information. Tandem mass spectrometry can be used to identify the sequence of a peptide and hence full or partial length proteins according to the methods disclosed herein. Precursor ions can be activated (with increased internal energy) in many different ways. Fragmentation patterns depend on how energy is transferred to the precursor ion, the amount of energy transferred, and how the transferred energy is internally distributed. Collision-induced dissociation and infrared multiphoton dissociation are "slow-heating" techniques that increase the Boltzmann temperature of the ion and thus preferentially cleave the weakest bonds.

The terms "peptide," "protein" and "polypeptide" refer, interchangeably, to a polymer of amino acids and/or amino acid analogs that are joined by peptide bonds or peptide bond mimetics. The twenty naturally-occurring amino acids and their single-letter and three-letter designations are as follows: Alanine A Ala; Cysteine C Cys; Aspartic Acid D Asp; Glutamic acid E Glu; Phenylalanine F Phe; Glycine G Gly; Histidine H His; Isoleucine I He; Lysine K Lys; Leucine L Leu; Methionine M Met; Asparagine N Asn; Proline P Pro; Glutamine Q Gln; Arginine R Arg; Serine S Ser; Threonine T Thr; Valine V Val; Tryptophan w Trp; and Tyrosine Y Tyr.

References to a mass of an amino acid means the monoisotopic mass or average mass of an amino acid at a given isotopic abundance, such as a natural abundance. In some examples, the mass of an amino acid can be skewed, for example, by labeling an amino acid with an isotope. Some degree of variability around the average mass of an amino acid is expected for individual single amino acids based on the exact isotopic composition of the amino acid.

The masses, including monoisotopic and average masses for amino acids are easily obtainable by one of ordinary skill the art.

Similarly, references to a mass of a peptide or protein means the monoisotopic mass or average mass of a peptide or protein at a given isotopic abundance, such as a natural abundance. In some examples, the mass of a peptide can be skewed, for example, by labeling one or more amino acids in the peptide or protein with an isotope. Some degree of variability around the average mass of a peptide is expected for individual single peptides based on the exact isotopic composition of the peptide. The mass of a particular peptide can be determined by one of ordinary skill the art.

A "vector," as used herein, refers to a recombinant plasmid or virus that comprises a nucleic acid to be delivered into a host cell, either in vitro or in vivo.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the nucleic acid can comprise sugars and phosphate groups (as may typically be found in RNA or DNA), or modified or substituted sugar or phosphate groups.

Alternatively, the backbone of the nucleic acid can comprise a polymer of synthetic subunits such as phosphoramidates and thus can be an oligodeoxynucleoside phosphoramidate (P-NH2) or a mixed phosphoramidate-phosphodiester oligomer. In addition, a double-stranded nucleic acid can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

A "recombinant viral vector" refers to a recombinant polynucleotide vector including one or more heterologous sequences (i.e., nucleic acid sequence not of viral origin).

A "recombinant AAV vector (rAAV vector)" refers to a polynucleotide vector including one or more heterologous sequences (i.e., nucleic acid sequence not of AAV origin) that may be flanked by at least one, for example, two, AAV inverted terminal repeat sequences (ITRs). Such rAAV vectors can be replicated and packaged into infectious viral particles when present in a host cell that has been infected with a suitable helper virus (or that is expressing suitable helper functions) and that is expressing AAV rep and cap gene products (i.e., AAV Rep and Cap proteins).

A "viral particle" refers to a viral particle composed of at least one viral capsid protein and an encapsulated viral genome.

"Heterologous" means derived from a genotypically distinct entity from that of the rest of the entity to which it is compared or into which it is introduced or incorporated. For example, a nucleic acid introduced by genetic engineering techniques into a different cell type is a heterologous nucleic acid (and, when expressed, can encode a heterologous polypeptide). Similarly, a cellular sequence (e.g., a gene or portion thereof) that is incorporated into a viral vector is a heterologous nucleotide sequence with respect to the vector.

An "inverted terminal repeat" or "ITR" sequence is relatively short sequences found at the termini of viral genomes which are in opposite orientation. An "AAV inverted terminal repeat (ITR)" sequence, is an approximately 145-nucleotide sequence that is present at both termini of a single-stranded AAV genome.

The term "hydrophilic interaction chromatography" or HILIC is intended to include a process employing a hydrophilic stationary phase and a hydrophobic organic mobile phase in which hydrophilic compounds are retained longer than hydrophobic compounds. In certain embodiments, the process utilizes a water-miscible solvent mobile phase.

The term "sample," as used herein, refers to a mixture of molecules that comprises at least a viral particle, such as an AAV particle, that is subjected to manipulation in accordance with the methods of the invention, including, for example, separating, analyzing, extracting, concentrating, profiling and the like.

The term "chromatographic surface," as used herein, includes a surface which is exposed to a sample or analytes. A chromatographic surface can be chemically modified, functionalized or activated or have a microstructure, for example, a pore. In certain embodiments, the chromatographic surface can be hydrophobic, hydrophilic (polar) or ionic. In other embodiments, the chromatographic surface is fully porous, superficially porous or non-porous.

The term "chromatographic core," as used herein, includes a chromatographic material, including but not limited to an organic material such as silica, in the form of a particle, a monolith or another suitable structure, which forms an internal portion of the materials of the invention. In certain aspects, the surface of the chromatographic core represents the chromatographic surface, or represents a material encased by a chromatographic surface, as defined herein. The chromatographic surface material may be disposed on or bonded to or annealed to the chromatographic core in such a way that a discrete or distinct transition is discernible or may be bound to the chromatographic core in such a way as to blend with the surface of the chromatographic core resulting in a gradation of materials and no discrete internal core surface. In certain aspects, the chromatographic surface material may be the same or different from the material of the chromatographic core and may exhibit different physical or physiochemical properties from the chromatographic core, including, but not limited to, pore volume, surface area, average pore diameter, carbon content or hydrolytic pH stability.

The term "hydrophilic," as used herein, describes having an affinity for, attracting, adsorbing or absorbing water.

The term "hydrophobic," as used herein, describes lacking an affinity for, repelling, or failing to adsorb or absorb water.

"Chromatography," as used herein, refers to the process of separating a mixture, for example a mixture containing viral capsid proteins. It involves passing a mixture through a stationary phase, which separates molecules of interest from other molecules in the mixture and allows one or more molecules of interest to be isolated. An example of a method of chromatographic separation is hydrophilic interaction liquid chromatography (HILIC).

"Contacting," as used herein, includes bringing together at least two substances in solution or solid phase, for example contacting a stationary phase of a chromatography material with a sample, such as a sample comprising viral particles.

General Description

Pompe disease is an autosomal recessive lysosomal storage disorder caused by mutations in the GAA gene encoding acid α-glucosidase (GAA)—a lysosomal enzyme responsible for the hydrolysis of glycogen to glucose. Deficiency in GAA results in accumulation of glycogen in lysosomes and subsequent cellular dysfunction in cardiac, skeletal, and smooth muscles as well as in the central nervous system. Pompe disease can present early in life as infantile onset Pompe disease (IOPD) or later in childhood to adulthood as late onset Pompe disease (LOPD). Respiratory failure is a prominent cause of death in both types of Pompe disease.

Figure 1:
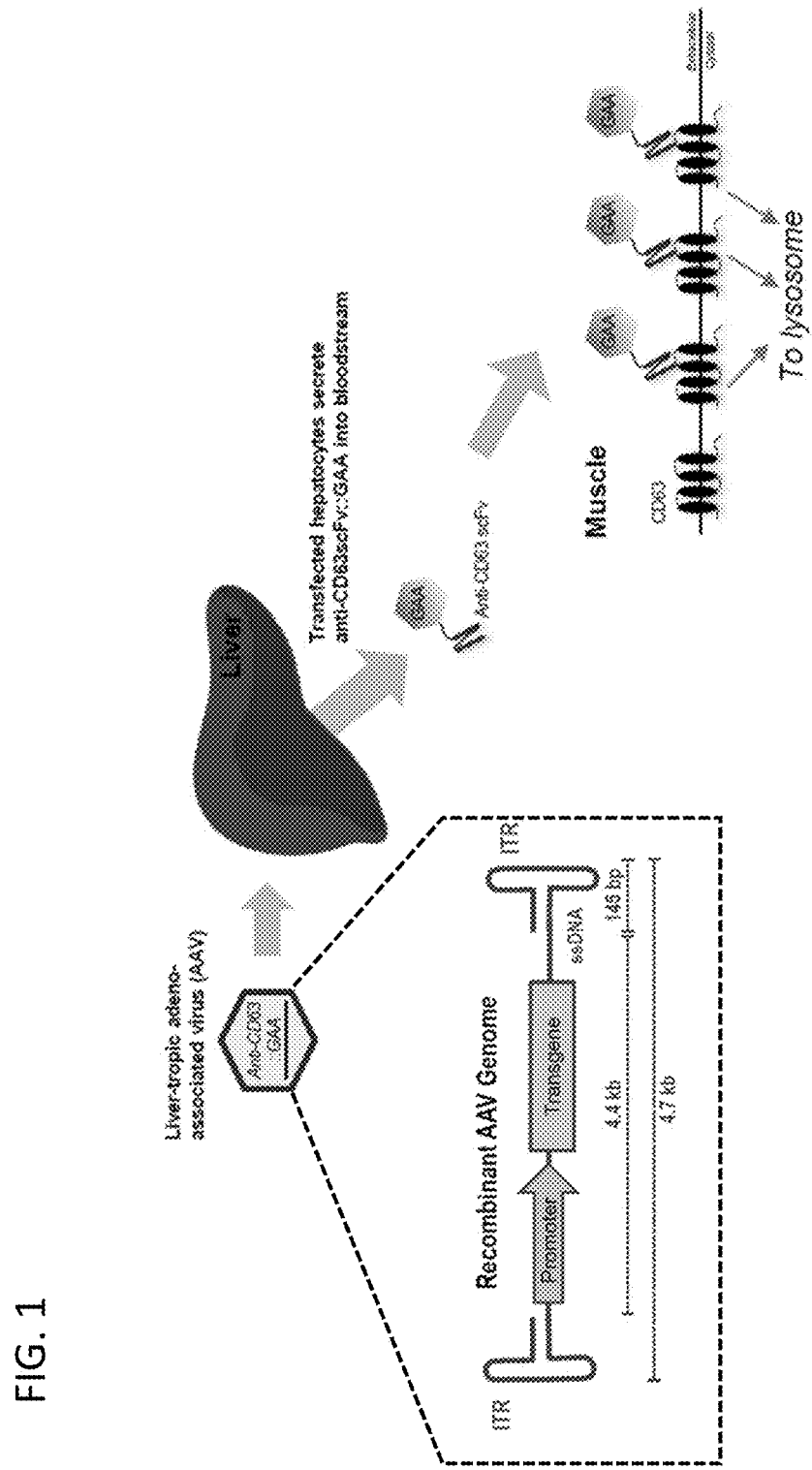
FIG. 1 is a schematic model of a possible treatment regimen for Pompe disease that includes the use of a Adeno-Associated Virus (AAV) as a Vector for Gene Therapy.

Currently, the only Food and Drug Administration approved treatment for Pompe disease is enzyme replacement therapy (ERT). However, systemically administered GAA does not cross the blood-brain barrier and therefore cannot treat the CNS pathology and affected respiratory motor neurons. Furthermore, ERT only partially corrects skeletal muscle abnormalities as a result of low uptake into muscle fibers. Consequently, two-thirds of IOPD patients eventually require ventilator support, and respiratory insufficiency persists among LOPD patients Gene therapy using adeno-associated virus (AAV) vectors is ideal for Pompe disease, since it is a monogenetic disorder. One of the strategies that is being studied is the combination of enzyme replacement with linked antibodies. In one example, high expression of anti-CD63::GAA from the liver via gene therapy is being developed to overcome the immune response to replacement enzyme seen in patients with no endogenous enzyme (see FIG. 1). As with all viral vector systems, it is important to ensure that the therapeutic composition contains the right amount of correctly formed viral particles. Thus, determining stoichiometry and protein composition of viral particles is very important Aspects of this disclosure are directed to a method of determining the stoichiometry of protein components of a viral capsid of a viral particle. In embodiments, the method includes subjecting a sample of viral particles to hydrophilic interaction liquid chromatography (HILIC) to separate the protein components of the viral capsid of the viral particles, such as viral particles of interest where information about the capsid is desired. In exemplary embodiments, an HILIC column is contacted with the sample containing the viral particles. In certain exemplary aspects, the method includes determining the masses of protein components of the viral capsid to identify the protein components separated by HILIC, for example, using mass spectrometry techniques, such as those described herein. In exemplary aspects, the method includes calculating the relative abundance of the protein components of the viral capsid from the HILIC separation to determine the stoichiometry of protein components of a viral capsid of a viral particle, for example using ultraviolet (UV) detection of the protein components of the viral capsid as they are eluted from the HILIC column. For example, the area of a UV peak can be used to determine the relative abundance of the capsid proteins and used to calculate the stoichiometry of the capsid proteins in the vital capsid (see e.g., FIG. 4). In another example, the peak height and/or peak UV intensity is used to determine relative abundance. In some embodiments, the retention time of the different proteins on the HILIC column is determined as a function of the mobile phase used and, in subsequent analysis this retention time can be used to determine the proteins and relative abundance of the proteins from the viral particle without the need to determine the mass and/or identity of the proteins every time a determination of stoichiometry is made, for example a standard value or values can be developed. Prior to this disclosure it was very difficult to resolve the different capsid proteins using conventional chromatography techniques (see e.g., FIGS. 3A and 3B). Using the sample conditions discussed herein for HILIC, good separation was achieved for AAV viral particles. In addition, the use of the HILIC column removed any requirement for a denaturation step. In certain aspects, the method is used to determine the serotype of a viral particle. For example, the masses of VP 1, VP2 and VP3 of each AAV serotype are unique and can be used to identify or differentiate AAV capsid serotypes. In addition, the separated capsid proteins can be subjected to downstream analysis, such as a determination of protein sequence and post-translational modifications of the capsid proteins, for example with accurate mass measurement at the intact protein level.

Aspects of this disclosure are directed a method of determining the heterogeneity of protein components in a capsid of a viral particle. In exemplary embodiments, the method includes subjecting the viral particle to HILIC to separate protein components of the viral particle capsid. In exemplary aspects, the method includes determining the masses of protein components of the protein capsid. In some cases, the masses of the protein components of the viral particle capsid are compared with theoretical masses of the viral particle capsid. A deviation of one or more of the masses of protein components of the viral particle capsid indicates that one or more proteins of the capsid are heterogeneous (see e.g., FIG. 5A). Conversely, no deviation would indicate that the proteins of the capsid are homogeneous (see e.g., FIGS. 5B-5D). In exemplary aspects, heterogeneity is due to one or more of mixed serotypes, variant capsids, capsid amino acid substitutions, truncated capsids, or modified capsids. In some aspects, the determination of the stoichiometry of protein components of a viral capsid of a viral particle and the determination of the heterogeneity of protein components in a capsid of a viral particle are done on the same sample, for example in a single test.

In one aspect, the present application provides a method for separating and/or characterizing capsid viral proteins, such as VP1, VP2, and VP3, from recombinant adeno-associated virus (AAV) using HILIC including a wide-pore amide-bonded column. The HILIC method can achieve greatly improved separation of capsid viral proteins from a variety of AAV serotypes using a generic method prior to MS detection. The present application provides an intact protein mass method for AAV capsid protein characterization, which utilized the unique selectivity of HILIC, followed by both fluorescence (FLR) and MS detection, for example, a HILIC-FLR-MS method. The HILIC-FLR-MS method of the present application can be used to characterize capsid proteins of viral particles including determining capsid identity, determining capsid heterogeneity, confirming serotype, assessing stoichiometry and identifying PTMs. The HILIC-FLR-MS method is shown to be particularly sensitive for capsid heterogeneity characterization by separating capsid protein variants resulting from different PTMs, such as phosphorylation, oxidation or protein backbone clippings. In particular, the HILIC-FLR-MS method of the present application can be generically applied to a variety of AAV serotypes without any sample treatment. In a single step, this HILIC-FLR-MS method provides confident AAV serotype confirmation, stoichiometry assessment, and PTM identification using low concentrations of AAV sample, such as about 30 ng protein on column, without any sample treatment. It is particular advantageous that the HILIC-FLR-MS method can be directly applied to AAV samples at extremely low concentrations without any sample treatment. Due to the higher throughput and reduced sample processing, this method is a valuable alternative to bottom-up based approach and provide characterization of capsid heterogeneity at intact protein levels.

In one aspect, the present application provides a method to improve the sensitivity of HILIC by combining HILIC with fluorescent detection which detects intrinsic fluorescence of tryptophan in capsid viral proteins. In one aspect, the present application provides a method to increase the amount of sample loading for HILIC analysis without reducing the sensitivity of HILIC analysis. In one aspect, the present application provides a method to improve the sensitivity of mass spectrometry analysis using desolvation gas modification device to mitigate ion suppression effect resulted from the use of trifluoroacetic acid (TFA) as the ion-pairing reagent in HILIC. The retention mechanism of HILIC is complex and primarily based on the partitioning of analytes between the high organic mobile phase and the water layer enriched on the stationary phase (Song, H.; Adams, E.; Desmet, G.; Cabooter, D. *J Chromatogr A* 2014, 1369, 83-91; D'Atri, V.; Fekete, S.; Beck, A.; Lauber, M.; Guillarme, D. *Analytical chemistry* 2017, 89, 2086-2092; Periat, A.; Fekete, S.; Cusumano, A.; Veuthey, J. L.; Beck, A.; Lauber, M.; Guillarme, D. *J Chromatogr A* 2016, 1448, 81-92).

In certain aspects, the viral particle is an AAV particle and the methods disclosed can be used to determine the stoichiometry of protein components in a capsid of an AAV particle and/or heterogeneity of protein components in a capsid of a AAV particle. In certain aspects, the protein components of the protein capsid comprise VP1, VP2 and VP3 of an AAV particle. In other aspects, the AAV particle is a recombinant AAV (rAAV) particle. The AAV particle includes an AAV vector encoding a heterologous transgene. In some aspects, a determined or calculated mass of the present disclosure (e.g., the determined or calculated mass of VP1, VP2 and/or VP3 of the AAV particle) may be compared with a reference, for example, a theoretical mass of a VP1, VP2, and/or VP3 of one or more AAV serotypes (see, for example, FIGS. 2A and 2B). A reference may include a theoretical mass of a VP1, VP2, and/or VP3 of one or more of any of the AAV serotypes. For example, in some aspects, the masses of VP1, VP2, and/or VP3 are compared to theoretical masses of one or more of an AAV1 capsid, an AAV2 capsid, an AAV3 capsid, an AAV4 capsid, an AAV5 capsid, an AAV6 capsid, an AAV7 capsid, an AAV8 capsid, an AAVrh8 capsid, an AAV9 capsid, an AAV 10 capsid, an AAV 11 capsid, an AAV 12 capsid, or a variant thereof. In some embodiments, a determined or calculated mass (e.g., the determined or calculated mass of VP1, VP2 and/or VP3 of the AAV particle) may be compared with a theoretical mass of a VP1, VP2, and/or VP3 of the corresponding AAV serotype.

In some aspects, the methods of the present disclosure may include determining the heterogeneity of the proteins of an AAV particle. In some aspects, a deviation of one or more of the masses of VP1, VP2 and/or VP3 (e.g., from a reference mass, such as a theoretical, predicted, or expected mass) is indicative of the AAV capsid protein heterogeneity. In some aspects, heterogeneity may include one or more of the following, without limitation: mixed serotypes, variant capsids, capsid amino acid substitutions, truncated capsids, or modified capsids.

In some exemplary embodiments, a method of determining the heterogeneity of an AAV particle may include subjecting a denatured AAV particle to LC/MS (e.g., as described herein), determining the masses of VP1, VP2 and VP3 of the AAV particle, and comparing these masses with theoretical masses of VP1, VP2 and VP3 of the AAV serotype; as well as subjecting fragments of VP1, VP2 and/or VP3 to LC/MS/MS, determining the masses of fragments of VP1, VP2 and VP3 of the AAV particle, and comparing these masses with theoretical masses of VP1, VP2 and VP3 of the AAV serotype (a deviation of one or more of the masses of VP1, VP2 or VP3 are indicative of the AAV capsid heterogeneity).

In certain aspects, the AAV particle includes an AAV1 capsid, an AAV2 capsid, an AAV3 capsid, an AAV4 capsid, an AAV5 capsid, an AAV6 capsid, an AAV7 capsid, an AAV8 capsid, an AAVrh8 capsid, an AAV9 capsid, an AAV10 capsid, an AAV11 capsid, an AAV 12 capsid, or a variant thereof.

In certain aspects, the masses of VP1, VP2, and VP3 are compared to theoretical masses of one or more of an AAV1 capsid, an AAV2 capsid, an AAV3 capsid, an AAV4 capsid, an AAV5 capsid, an AAV6 capsid, an AAV7 capsid, an AAV8 capsid, an AAVrh8 capsid, an AAV9 capsid, an AAV10 capsid, an AAV11 capsid, an AAV 12 capsid, or a variant thereof.

In certain aspects, the AAV particle comprises an AAV1 ITR, an AAV2 ITR, an AAV3 ITR, an AAV4 ITR, an AAV5 ITR, an AAV6 ITR, an AAV7 ITR, an AAV8 ITR, an AAVrh8 ITR, an AAV9 ITR, an AAV 10 ITR, an AAV11 ITR, or an AAV 12 ITR.

In other aspects, the AAV particle has a capsid serotype selected for transduction of cells of a subject's liver. In other aspects, the AAV particle has a capsid serotype AAV7, AAV8, or AAV9, which are selective for the transduction of cells of a subject's liver.

In yet other aspects, the AAV particle is a recombinant AAV (rAAV) particle. In some aspects, the AAV particle comprises an AAV vector encoding a heterologous transgene. In some aspects, the AAV particle has a capsid serotype AAV7, AAV8, or AAV9. In some aspects, the AAV particle has a capsid serotype AAV9 and is a viral vector encoding Lysosomal Alpha Glucosidase (GAA) linked to an antibody specific for an antigen expressed from a muscle cell (e.g., an anti-CD63 antibody).

While AAV was the model viral particle for this disclosure, it is contemplated that the disclosed methods can be applied to profile a variety of viruses, for example, the viral families, subfamilies, and genera. The methods of the present disclosure may find use, for example, in profiling VPs to monitor VP expressions, posttranslational modifications, and truncations and to ensure product consistency during VLP production, to confirm site-direct mutagenesis or structural characterization for capsid protein engineering applications, and/or to monitor or detect heterogeneity of a viral particle or preparation.

In exemplary embodiments, the viral vector encodes a heterologous transgene.

In exemplary embodiments, the viral particle belongs to a viral family selected from the group consisting of Adenoviridae, Parvoviridae, Retroviridae, Baculoviridae, and Herpesviridae.

In certain aspects, the viral particle belongs to a viral genus selected from the group consisting of Atadenovirus, Aviadenovirus, Ichtadenovirus, Mastadenovirus, Siadenovirus, Ambidensovirus, Brevidensovirus, Hepandensovirus, Iteradensovirus, Penstyldensovirus, Amdoparvovirus, Aveparvovirus, Bocaparvovirus, Copiparvovirus, Dependoparvovirus, Erythroparvovirus, Protoparvovirus, Tetraparvovirus, Alpharetrovirus, Betaretrovirus, Deltaretrovirus, Epsilonretrovirus, Gammaretrovirus, Lentivirus, Spumavirus, Alphabaculovirus, Betabaculovirus, Deltabaculovirus, Gammabaculovirus, Iltovirus, Mardivirus, Simplexvirus, Varicellovirus, Cytomegalovirus, Muromegalovirus, Proboscivirus, Roseolovirus, Lymphocryptovirus, Macavirus, Percavirus, and Rhadinovirus.

In certain aspects, the Retroviridae is Moloney murine sarcoma virus (MoMSV), Harvey murine sarcoma virus (HaMuSV), murine mammary tumor virus (MuMTV), gibbon ape leukemia virus (GaLV), feline leukemia virus (FLV), Spumavirus, Friend virus, Murine Stem Cell Virus (MSCV) Rous Sarcoma Virus (RSV), human T cell leukemia viruses, Human Immunodeficiency Viruse (HIV), feline immunodeficiency virus (FIV), equine immunodeficiency virus (EIV), visna-maedi virus; caprine arthritis-encephalitis virus; equine infectious anemia virus; feline immunodeficiency virus (FIV); bovine immune deficiency virus (BIV); or simian immunodeficiency virus (SIV).

Hydrophilic interaction chromatography (HILIC) is a variant of NP-HPLC that can be performed with partially aqueous mobile phases, permitting normal-phase separation of peptides, carbohydrates, nucleic acids, and many proteins. The elution order for HILIC is least polar to most polar, the opposite of that in reversed-phase HPLC.

HILIC separates analytes based on polar interactions between the analytes and the stationary phase (e.g., substrate). The polar analyte associates with and is retained by the polar stationary phase. Adsorption strengths increase with increases in analyte polarity, and the interaction between the polar analyte and the polar stationary phase (relative to the mobile phase) increases the elution time. Use of more polar solvents in the mobile phase will decrease the retention time of the analytes, while more hydrophobic solvents tend to increase retention times.

Various types of substrates can be used with HILIC, for example, for column chromatography, including silica, amino, amide, cellulose, cyclodextrin and polystyrene substrates. Examples of useful substrates, for example, that can be used in column chromatography, include: polySulfoethyl Aspartamide (e.g., from PolyLC), a sulfobetaine substrate, e.g., ZIC®-HILIC (e.g., from SeQuant), POROS® HS (e.g., from Applied Biosystems), POROS® S (e.g., from Applied Biosystems), PolyHydroethyl Aspartamide (e.g., from PolyLC), Zorbax 300 SCX (e.g., from Agilent), PolyGLY-COPLEX® (e.g., from PolyLC), Amide-80 (e.g., from Tosohaas), TSK GEL® Amide-80 (e.g., from Tosohaas), Polyhydroxyethyl A (e.g., from PolyLC), Glyco-Sep-N (e.g., from Oxford GlycoSciences), and Atlantis HILIC (e.g., from Waters). Columns that can be used in the disclosed methods include columns that utilize one or more of the following functional groups: carbamoyl groups, sulfopropyl groups, sulfoethyl groups (e.g., poly (2-sulfoethyl aspartamide)), hydroxyethyl groups (e.g., poly (2-hydroxyethyl aspartamide)) and aromatic sulfonic acid groups.

In certain aspects, the capsid proteins are separated on the HILIC column and subsequently eluted from the HILIC column, for example using a mobile phase gradient to resolve the individual capsid proteins, thereby purifying and or separating capsid proteins in the sample. In certain examples, the eluted capsid proteins from the HILIC column are separated into one or more fractions. Such fractions can be used for subsequent analysis, such as MS analysis. In certain embodiments, the methods include identifying capsid proteins present in one or more of the fractions.

The mobile phase used may include buffers with and without ion pairing agents, e.g., acetonitrile and water. Ion pairing agents include formate, acetate, TFA (trifluoroacetic acid) and salts. Gradients of the buffers can be used, for example, if two buffers are used, the concentration or percentage of the first buffer can decrease while the concentration or percentage of the second buffer increases over the course of the chromatography run. For example, the percentage of the first buffer can decrease from about 100%, about 99%, about 95%, about 90%, about 85%, about 80%, about 75%, about 70%, about 65%, about 60%, about 50%, about 45%, or about 40% to about 0%, about 1%, about 5%, about 10%, about 15%, about 20%, about 25%, about 30%, about 35%, or about 40% over the course of the chromatography run. As another example, the percentage of the second buffer can increase from about 0%, about 1%, about 5%, about 10%, about 15%, about 20%, about 25%, about 30%, about 35%, or about 40% to about 100%, about 99%, about 95%, about 90%, about 85%, about 80%, about 75%, about 70%, about 65%, about 60%, about 50%, about 45%, or about 40% over the course of the same run. In certain aspects, the proportion of mobile phase A in the chromatography increases over time. Optionally, the concentration or percentage of the first and second buffer can return to their starting values at the end of the chromatography run. As an example, the percentage of the first buffer can change in five steps from 85% to 63% to 59% to 10% to 85%; while the percentage of the second buffer in the same steps changes from 15% to 37% to 41% to 90% to 15%. The percentages can change gradually as a linear gradient or in a non-linear (e.g., stepwise) fashion. For example, the gradient can be multiphasic, for example, biphasic, triphasic, etc. In preferred aspects, the methods described herein use a decreasing acetonitrile buffer gradient which corresponds to increasing polarity of the mobile phase without the use of ion pairing agents. In aspects, the HILIC uses a mobile phase A comprising trifluoroacetic acid in water. In other aspects, the mobile phase A comprises about 0.1% trifluoroacetic acid. In embodiments, the chromatography comprises a mobile phase B comprising trifluoroacetic acid in acetonitrile. In embodiments, the mobile phase B comprises about 0.1% trifluoroacetic acid.

The column temperature can be maintained at a constant temperature throughout the chromatography run, for example, using a commercial column heater. In some aspects, the column is maintained at a temperature between about 50° C. to about 70° C., e.g., about 50° C. to about 60° C., about 55° C. to about 60° C., e.g., at about 50° C., about 55° C., about 60° C., about 65° C., or about 70° C. In one aspect, the temperature is about 60° C.

The flow rate of the mobile phase can be between about 0 to about 100 ml/min. For analytical proposes, flow rates typically range from 0 to 10 ml/min, for preparative HPLC, flow rates in excess of 100 ml/min can be used. For example, the flow rate can be about 0.5, about 1, about 1.5, about 2, about 2.5, about 3, about 3.5, about 4, about 4.5, or about 5 ml/min. Substituting a column having the same packing, the same length, but a smaller diameter requires a reduction in the flow rate in order to maintain the same retention time and resolution for peaks as seen with a column of wider diameter. Preferably, a flow rate equivalent to about 1 ml/min in a 4.6×100 mm, 5 µm column is used.

The run time can be between about 15 to about 240 minutes, for example, about 20 to about 70 min, about 30 to about 60 min, about 40 to about 90 min, about 50 min to about 100 min, about 60 to about 120 min, about 50 to about 80 min. In embodiments, the mobile phase A increases from about 15% to about 100%, over about 45 minutes.

In some exemplary embodiments, the methods include subjecting a viral particle to liquid chromatography/mass spectrometry (LC/MS). As is known in the art, LC/MS utilizes liquid chromatography for physical separation of ions and mass spectrometry for generation of mass spectral data from the ions. Such mass spectral data may be used to determine, for example, molecular weight or structure, identification of particles by mass, quantity, purity, and so forth.

These data may represent properties of the detected ions such as signal strength (e.g., abundance) over time (e.g., retention time), or relative abundance over mass-to-charge ratio.

In some aspects, mass spectrometry (e.g., used in LC/MS as described herein) may refer to electrospray ionization mass spectrometry (ESI-MS). ESI-MS is known in the art as a technique that uses electrical energy to analyze ions derived from a solution using mass spectrometry (see, e.g., Yamashita, M. and Fenn, J. B. (1984). Phys. Chem. 88:4451-4459). Ionic species, including neutral species that are ionized in solution or in gaseous phase, are transferred from a solution to a gaseous phase by dispersal in an aerosol of charged droplets. Subsequently, solvent evaporation is conducted to reduce the size of the charged droplets. Then, sample ion is ejected from the charge droplets as the solution passing through a small capillary with a voltage relative to ground. For example, the wall of the surrounding ESI chamber is performed by mixing the sample with volatile acid and organic solvent and infusing it through a conductive needle charged with high voltage. The charged droplets that are sprayed (or ejected) from the needle end are directed into the mass spectrometer, and are dried up by heat and vacuum as they fly in. After the drops dry, the remaining charged molecules are directed by electromagnetic lenses into the mass detector and mass analyzed. In one aspect, the eluted sample is deposited directly from the capillary into an electrospray nozzle, for example, the capillary functions as the sample loader. In another aspect, the capillary itself functions as both the extraction device and the electrospray nozzle.

For MALDI, the analyte molecules (e.g., proteins) are deposited on metal targets and co-crystallized with an organic matrix. The samples are dried and inserted into the mass spectrometer, and typically analyzed via time-of-flight (TOF) detection. In one aspect, the eluted sample is deposited directly from the capillary onto the metal target, for example, the capillary itself functions as the sample loader. In one aspect, the extracted analyte is deposited on a MALDI target, a MALDI ionization matrix is added, and the sample is ionized and analyzed, for example, by TOF detection.

In some exemplary embodiments, other ionization modes are used for example, ESI-MS, turbospray ionization mass spectrometry, nanospray ionization mass spectrometry, thermospray ionization mass spectrometry, sonic spray ionization mass spectrometry, SELDI-MS and MALDI-MS. In general, an advantage of these methods is that they allow for the "just-in-time" purification of sample and direct introduction into the ionizing environment. It is important to note that the various ionization and detection modes introduce their own constraints on the nature of the desorption solution used, and it is important that the desorption solution be compatible with both. For example, the sample matrix in many applications must have low ionic strength, or reside within a particular pH range, etc. In ESI, salt in the sample can prevent detection by lowering the ionization or by clogging the nozzle. This problem can be addressed by presenting the analyte in low salt and/or by the use of a volatile salt. In the case of MALDI, the analyte should be in a solvent compatible with spotting on the target and with the ionization matrix employed.

In some exemplary embodiments, the methods include subjecting a viral particle of the present disclosure, or subjecting digested fragments of a denatured viral particle of the present disclosure, to liquid chromatography/mass spectrometry-mass spectrometry (LC/MS/MS). As is known in the art, LC/MS/MS (the term "liquid chromatography-tandem mass spectrometry" may be used interchangeably herein) utilizes liquid chromatography for physical separation of ions and mass spectrometry for generation of mass spectral data from the ions, where the mass spectrometry uses multiple stages of mass (e.g., m/z) separation, typically separated by a fragmentation step. For example, ions of interest within a range of m/z may be separated out in a first round of MS, fragmented, and then further separated based on individual m/z in a second round of MS. Ion fragmentation may include without limitation a technique such as collision-induced dissociation (CID), higher energy collision dissociation (HCD), electron-capture dissociation (ECD), or electron-transfer dissociation (ETD).

A variety of mass analyzers suitable for LC/MS and/or LC/MS/MS are known in the art, including without limitation time-of-flight (TOF) analyzers, quadrupole mass filters, quadrupole TOF (QTOF), and ion traps (e.g., a Fourier transform-based mass spectrometer or an Orbitrap). In Orbitrap, a barrel-like outer electrode at ground potential and a spindle-like central electrode are used to trap ions in trajectories rotating elliptically around the central electrode with oscillations along the central axis, confined by the balance of centrifugal and electrostatic forces. The use of such instruments employs a Fourier transform operation to convert a time domain signal (e.g., frequency) from detection of image current into a high resolution mass measurement (e.g., nano LC/MS/MS). Further descriptions and details may be found, for example, in Scheltema, R. A. et al. (2014) Mol. Cell Proteomics 13:3698-3708; Perry, R. H. et al. (2008) Mass. Spectrom. Rev. 27:661-699; and Scigelova, M. et al. (2011) Mo/. Cell Proteomics 10:M11 1.009431.

In some aspects, masses of viral capsid proteins may be determined, for example, based on LC/MS and/or LC/MS/MS data. In some aspects, masses of VP1, VP2 and VP3 of an AAV particle, or of fragments of VP1, VP2 and VP3 of the AAV particle, may be determined, for example, based on LC/MS and/or LC/MS/MS data. Various methods to determine protein mass and/or identity from MS data are known in the art. For example, peptide mass fingerprinting may be used to determine protein sequence based on MS data, or proteins may be identified based on MS/MS data related to one or more constituent peptides. When using tandem MS, product ion scanning may be used to analyze m/z data related to one or more peptides of a protein of interest. Software known in the art may then be used, for example, to match identified peaks to reference or known peaks, to group peaks into isotopomer envelopes, and so forth. Peptide mass values may be compared to a database of known peptide sequences. For example, Mascot may be used to match observed peptides with theoretical database peptides, for example, resulting from application of a particular digest pattern to an in silico protein database. Other suitable software may include without limitation Proteome Discoverer, ProteinProspector, X! Tandem, Pepfinder, Bonics, or MassLynx™ (Waters).

In some aspects, the heterologous nucleic acid is operably linked to a promoter. Exemplary promoters include, but are not limited to, the cytomegalovirus (CMV) immediate early promoter, the RSV LTR, the MoMLV LTR, the phosphoglycerate kinase-1 (PGK) promoter, a simian virus 40 (SV40) promoter and a CK6 promoter, a transthyretin promoter (TTR), a TK promoter, a tetracycline responsive promoter (TRE), an HBV promoter, an hAAT promoter, a LSP promoter, chimeric liver-specific promoters (LSPs), the E2F promoter, the telomerase (hTERT) promoter; the cytomegalovirus enhancer/chicken beta-actin/Rabbit β-globin promoter (CAG promoter; Niwa et al., Gene, 1991, 108(2): 193-9) and the elongation factor 1-alpha promoter (EF1-alpha) promoter (Kim et al., Gene, 1990, 91(2):217-23 and Guo et al., Gene Ther., 1996, 3(9): 802-10). In some aspects, the promoter comprises a human β-glucuronidase promoter or a cytomegalovirus enhancer linked to a chicken β-actin (CBA) promoter. The promoter can be a constitutive, inducible or repressible promoter. In some aspects, the invention provides a recombinant vector comprising a nucleic acid encoding a heterologous transgene of the present disclosure operably linked to a CBA promoter.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer), the SV40 promoter, the dihydrofolate reductase promoter, the 13-actin promoter, the phosphoglycerol kinase (PGK) promoter, and the EFla promoter.

Inducible promoters allow regulation of gene expression and can be regulated by exogenously supplied compounds, environmental factors such as temperature, or the presence of a specific physiological state, for example, acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268: 1766-1769 (1995), see also Harvey et al., Curr. Opin. Chem. Biol., 2:512-518 (1998)), the RU486-inducible system (Wang et al., Nat. Biotech., 15:239-243 (1997) and Wang et al, Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, for example, temperature, acute phase, a particular differentiation state of the cell, or in replicating cells only.

In another aspect, the native promoter, or fragment thereof, for the transgene will be used. The native promoter can be used when it is desired that expression of the transgene should mimic the native expression. The native promoter may be used when expression of the transgene must be regulated temporally or developmentally, or in a tissue-specific manner, or in response to specific transcriptional stimuli. In a further aspect, other native expression control elements, such as enhancer elements, polyadenylation sites or Kozak consensus sequences may also be used to mimic the native expression In some aspects, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art.

In some aspects, the vector comprises an intron. For example, in some embodiments, the intron is a chimeric intron derived from chicken beta-actin and rabbit beta-globin. In some aspects, the intron is a minute virus of mice (MVM) intron.

In some aspects, the vector comprises a polyadenylation (polyA) sequence. Numerous examples of polyadenylation sequences are known in the art, such as a bovine growth hormone (BGH) Poly(A) sequence (see, e.g., accession number EF592533), an SV40 polyadenylation sequence, and an HSV TK pA polyadenylation sequence.

The exemplary systems, methods, and acts described in the various embodiments presented previously are illustrative, and, in alternative exemplary embodiments, certain acts can be performed in a different order, in parallel with one another, omitted entirely, and/or combined between different exemplary embodiments, and/or certain additional acts can be performed, without departing from the scope and spirit of various embodiments and aspects. Accordingly, such alternative embodiments are included in the examples described herein.

Although specific exemplary embodiments have been described above in detail, the description is merely for purposes of illustration. It should be appreciated, therefore, that many aspects described above are not intended as required or essential elements unless explicitly stated otherwise. Modifications of, and equivalent components or acts corresponding to, the disclosed aspects of the example embodiments, in addition to those described above, can be made by a person of ordinary skill in the art, having the benefit of the present disclosure, without departing from the spirit and scope of embodiments defined in the following claims, the scope of which is to be accorded the broadest interpretation so as to encompass such modifications and equivalent structures.

The following examples are provided to illustrate particular features of certain exemplary embodiments. However, the particular features described below should not be considered as limitations on the scope of the invention, but rather as examples from which equivalents will be recognized by those of ordinary skill in the art.

EXAMPLE

The following example is put forth so as to provide those of ordinary skill in the art with a complete disclosure and description of how to make and use the methods of the invention, and is not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight unless indicated, temperature is in degrees Centigrade, room temperature is about 25° C., and pressure is at or near atmospheric.

Material and Methods

The AAV serotype samples included AAV1, AAV2, AAV6, AAV7, AAV8, AAV9, AAVhu37 and AAVDJ. Acetonitrile (ACN), trifluoroacetic acid (TFA), formic acid (FA), TCEP-HCl (tris (2-carboxyethyl) phosphine hydrochloride), and ultraPure 1 M Tris-HCl buffer pH 7.5 were purchased from Thermo Fisher Scientific (Waltham, Mass., USA). Propionic acid (PA), acetic acid, urea, and iodoacetamide were purchased from Sigma Aldrich, Co (St. Louis, Mo., USA). Isopropanol (IPA) was purchased from VWR International, LLC (Radnor, Pa., USA). Sequence grade modified trypsin was purchased from Promega (Madison, Wis., USA). Deionized water was provided by a Milli-Q integral water purification system installed with a MilliPak Express 20 filter (Millipore Sigma, Burlington, Mass., USA).

The liquid chromatography (LC) separation was performed on a Waters I-Class UPLC system (Waters, Milford, Mass., USA) equipped with a photodiode array (PDA) detector and a fluorescence (FLR) detector. Both HILIC and RPLC (reversed-phase liquid chromatography) modes utilized mobile phase A as 0.1% (v/v) TFA in water, mobile phase B as 0.1% (v/v) TFA in acetonitrile (ACN), a gradient flow rate of 0.2 mL/min and a column temperature of 60° C. for the elution of intact capsid proteins. For HILIC separation, 1 to 3 µL of each AAV sample was injected onto a Waters ACQUITY UPLC Glycoprotein BEH Amide Column (300 Å, 1.7 µm, 2.1×150 mm) either directly (1 µL) or using a loading strategy greater than 1 µL. One loading strategy was adjusting a larger aliquot of AAV stock solution (e.g., greater than 1 µL) with organic solvent to match the initial mobile phase conditions, and then injected in its entirety onto the HILIC column. An alternative loading strategy was the use of multiple sample loading steps by repeating 1 µL injections of the AAV samples onto the HILIC column before initiating the gradient for AAV capsid protein elution and separation. The gradient of the mobile phase of HILIC included an initial gradient hold at 85% mobile phase B for 0.5 min, 85% B to 70% B over the next 0.5 min, a 2 min hold at 70% B, then 70% B to 64% B in 16 minutes. The gradient was then set to 0% B over 1 min and held for 2 min for column washing, before ramping to 85% B in 0.5 min, and maintained at initial condition for 7.5 min to equilibrate the column for the next run.

For RPLC separation, 3 µL of each AAV sample was injected onto a Waters ACQUITY UPLC Protein BEH C4 column (300 Å, 1.7 µm, 2.1×150 mm). The gradient of the mobile phase of RPLC included an initial gradient hold at 20% mobile phase B for 3 min, 20% B to 35% B over the next 2 min, a 2 min hold at 35% B, then 35 to 55% B in 13 min, followed by a ramp to 95% B over 3 minutes and a 5 min washing step at 95% B before re-equilibrating to initial condition. For UV detection, the wavelength was set at 280 nm.

For FLR detection, excitation (Ex) and emission (Em) wavelengths of 280 and 348 nm were employed. The mass spectrometric analysis was performed on a Q-Exactive Plus Orbitrap mass spectrometer (Thermo Fisher Scientific, Bremen, Germany). The resolution was set at 17,500, the capillary spray voltage was set at 3.5 kV, the in-source fragmentation energy was set at 75, the S-lens RF level was set at 60, the source temperature was set at 250° C., and the capillary temperature was set at 350° C. Mass spectra were acquired with an m/z range window between 800 and 4000. To counteract TFA-induced ion suppression, a desolvation gas modification device, delivering a dopant gas containing a 3:1 (v/v) ratio of propionic acid (PA) and isopropanol (IPA), was implemented on the ion source (Wang, S.; Xing, T.; Liu, A. P.; He, Z.; Yan, Y.; Daly, T. J.; Li, N. *Analytical chemistry* 2019, 91, 3156-3162). The raw MS data was deconvoluted using Intact Mass™ software from Protein Metrics (Cupertino, Calif., USA).

Example 1

Separation of Capsid Proteins from Intact AAV Particles

Figure 4:
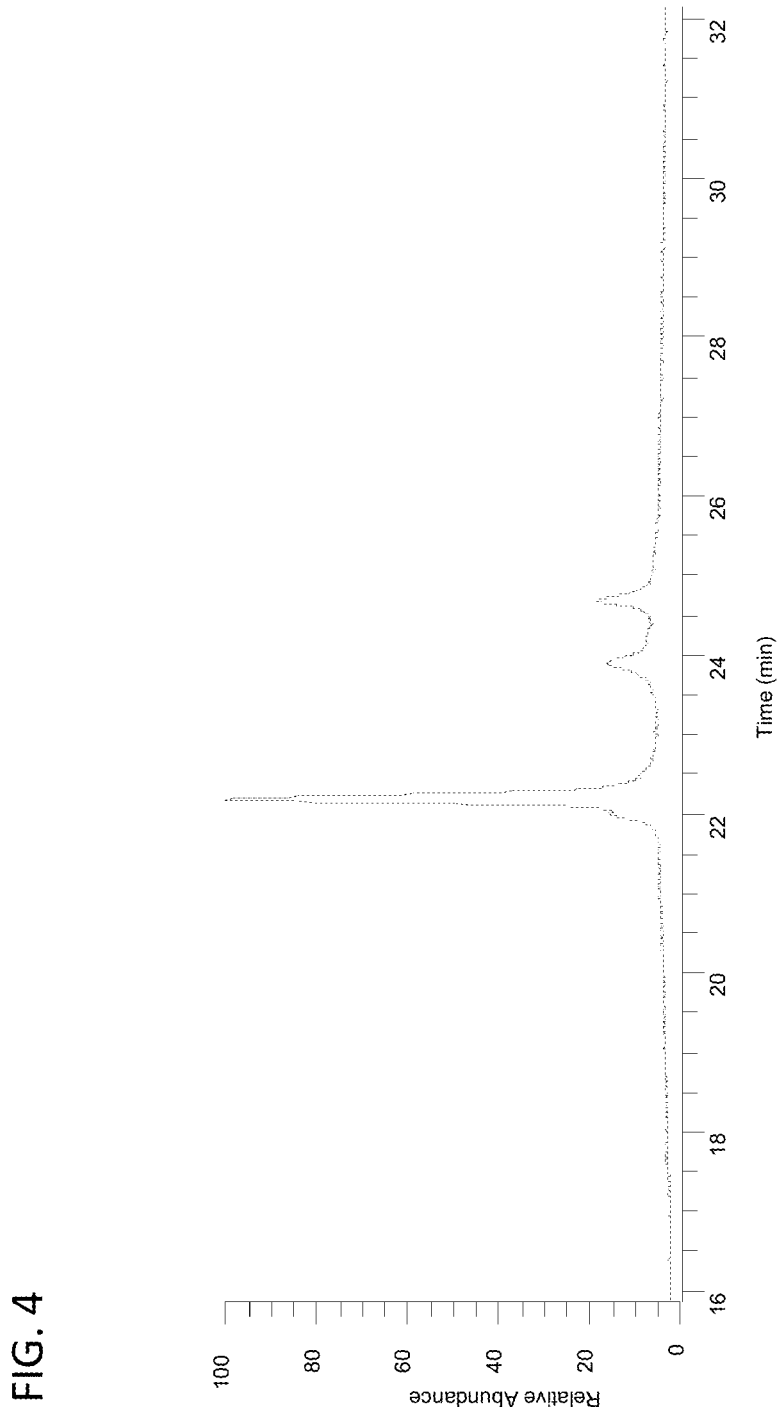
FIG. 4 is UV trace from a hydrophilic interaction liquid chromatography (HILIC) separation of AAV capsid proteins from an AAV particle showing high resolution of the individual proteins and the determination of the relative abundance of the individual proteins according to an exemplary embodiment.

For separation of an intact AAV9 viral particles, 1 µL of the AAV sample was injected onto a HILIC column, as described in the table below. The results of the separation are shown in FIG. 4. As shown, the three AAV capsid proteins showed complete resolution from each other.

Table 1 shows a summary of the chromatographic conditions used for the separation of AAV9 capsid proteins from an intact AAV9 capsid.

TABLE 1

Summary of chromatographic conditions

| | |
|---|---|
| UPLC System | Waters ACQUITY UPLC I-Class |
| Mobile Phase | A: 0.1% IFA in water |
| | B: 0.1% TFA in acetonitrile |
| Column | ACQUITY UPLC ® GlycoproteinBEH Amide 1.7 µm, 2.1 mm × 150 mm, Part No. 186007963 |
| Column Temperature | 60° C. ± 1° C. |
| Autosampler Temperature | 5° C. ± 2° C. |

| Gradient | Time (min) | Flow (mL/min) | % A | % B |
|---|---|---|---|---|
| | 0 | 0.2 | 15.0 | 85.0 |
| | 0.5 | 0.2 | 15.0 | 85.0 |
| | 1.0 | 0.2 | 25.0 | 75.0 |
| | 41.0 | 0.2 | 40.0 | 60.0 |
| | 42.0 | 0.2 | 100.0 | 0.0 |
| | 44.0 | 0.2 | 100.0 | 0.0 |
| | 45.0 | 0.2 | 15.0 | 85.0 |
| | 55.0 | 0.2 | 15.0 | 85.0 |

| | |
|---|---|
| Detector Wavelength | 280 nm |

Figure 3A:
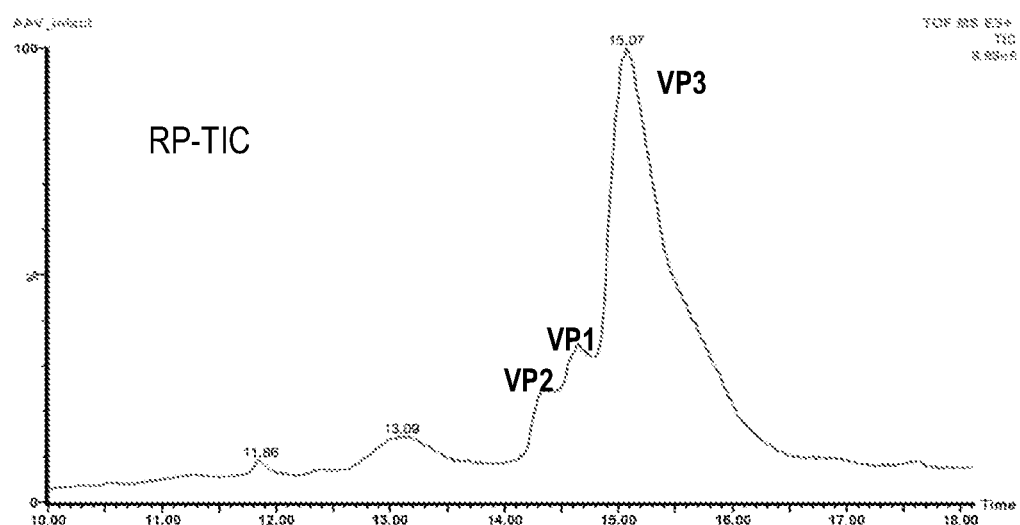
FIG. 3A is UV trace from a reverse phase TIC separation of AAV capsid proteins from an AAV particle showing poor resolution of the individual proteins.
Figure 3B:
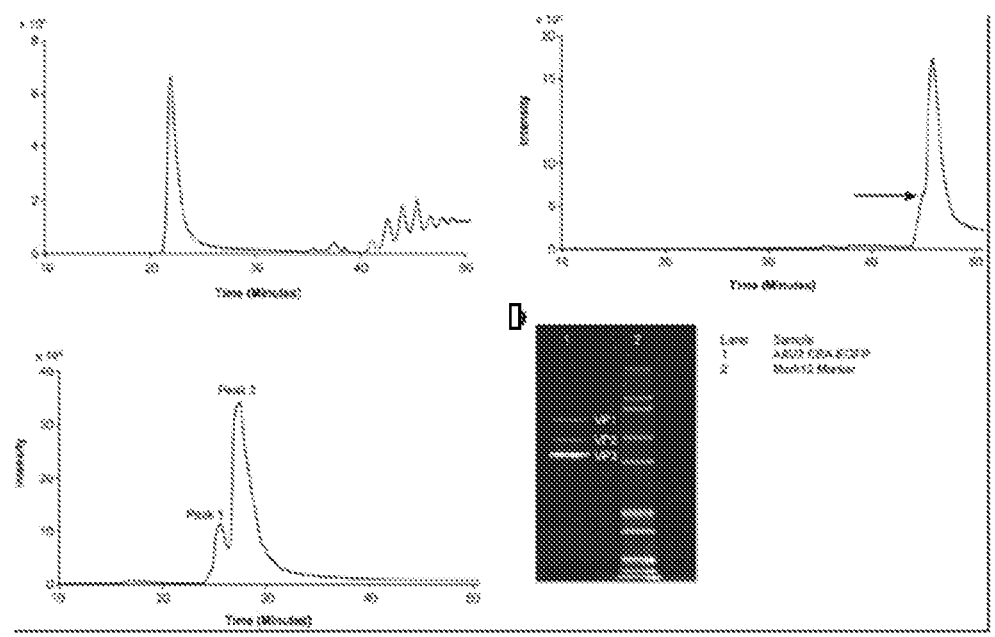
FIG. 3B is a comparison of several prior art separation methods showing both poor resolution and/or poor quantification.

Compared to RPLC-based separation, the unique retention mechanism of the HILIC column worked surprisingly better for the separations of viral particles or capsid viral proteins (see FIGS. 4, 3A and 3B).

Example 2

Mass Spectral Analysis of Separated AAV Capsid Proteins

One of the advantages of the methods described herein is that no sample preparation is required. 1 uL of the sample was directly injected into the into the LC-MS and the resulting data analyzed. The following tune parameters were applied on a Q-Exactive Plus mass spectrometer for intact mass analysis:

| | |
|---|---|
| Spray voltage | 3.5 kV |
| Capillary Temperature | 350° C. |
| S-lens RF level | 60 |
| Sheath Gas flow rate | 40 |
| Aux Gas flow rate | 15 |
| In-source CID | 0.0 eV |
| m/z range | 800-4000 |

Figure 5:
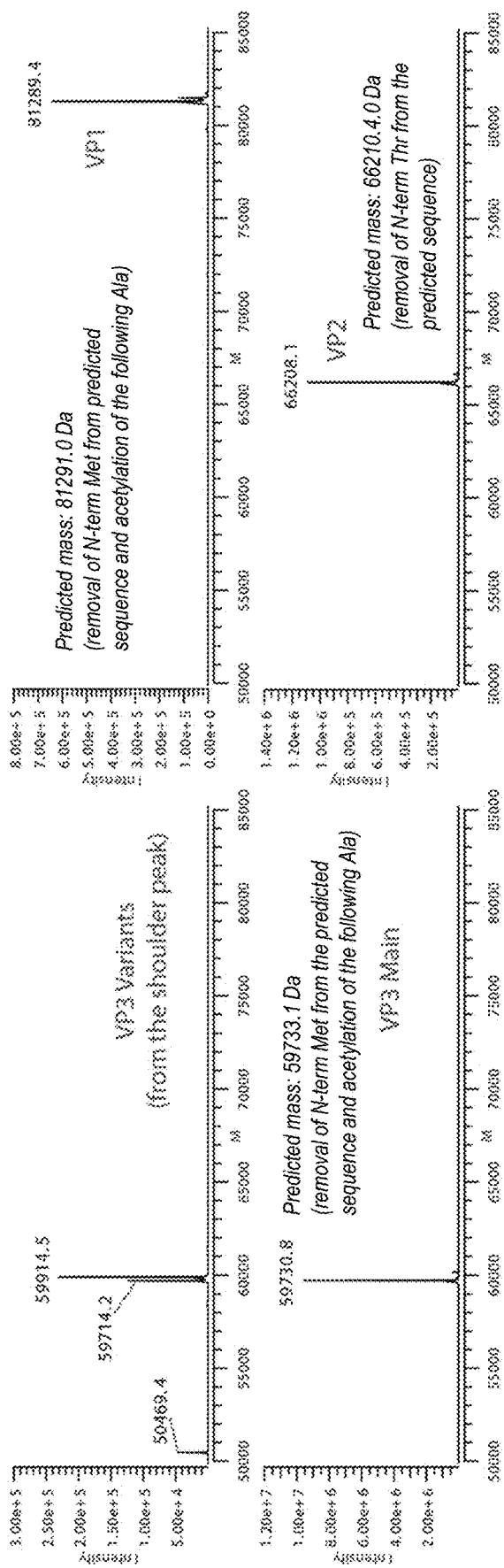
FIGS. 5A-5D are mass spectra of AAV capsid proteins from an AAV particle according to an exemplary embodiment.

FIGS. 5A-5D show mass spectra of the individual capsid proteins. As shown in FIG. 5A, there was protein heterogeneity in VP3.

Figure 6:
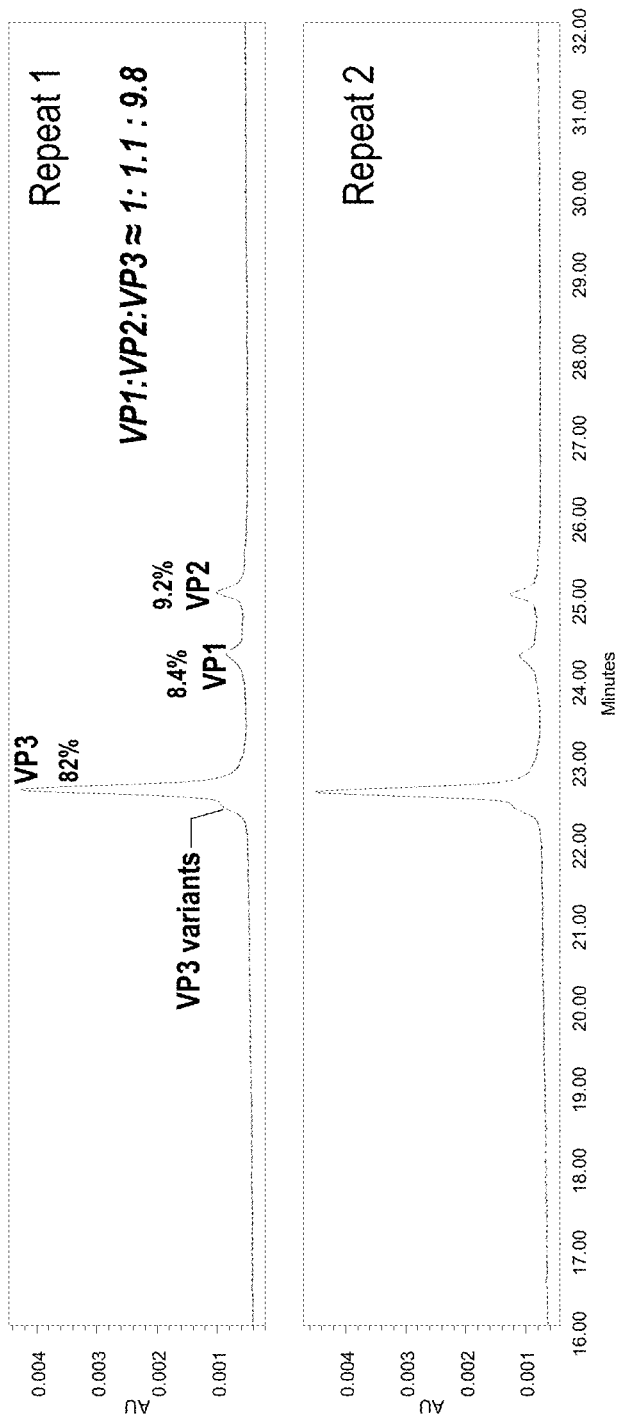
FIG. 6 shows two traces of HILIC-UV analysis of AAV9 viral particles and their stoichiometry determination according to an exemplary embodiment.

As shown in FIG. 6, the peak height can be used to determine the stoichiometry of the intact AAV particles.

Example 3

Comparison of HILIC and RPLC for Separating AAV Capsid Proteins

Capsid proteins from three AAV serotypes, for example, AAV6, AAV7, and AAV8, were separated by RPLC using a Protein BEH C4 column (300 Å, 1.7 µm, 2.1 mm×150 mm) or by HILIC using a Glycoprotein BEH amide column (300 Å, 1.7 µm, 2.1 mm×150 mm). The separations were followed by FLR and MS (mass spectrometry) detections. TFA was used as an ion-pairing reagent at 0.1% (v/v) in both separation modes. A comparable gradient steepness was applied in both methods for fair comparison. The intrinsic fluorescence of tryptophan was detected using FLR detection which was used to replace UV detection. The utilization of FLR detection provided improved sensitivity compared to UV detection.

Figure 7A:
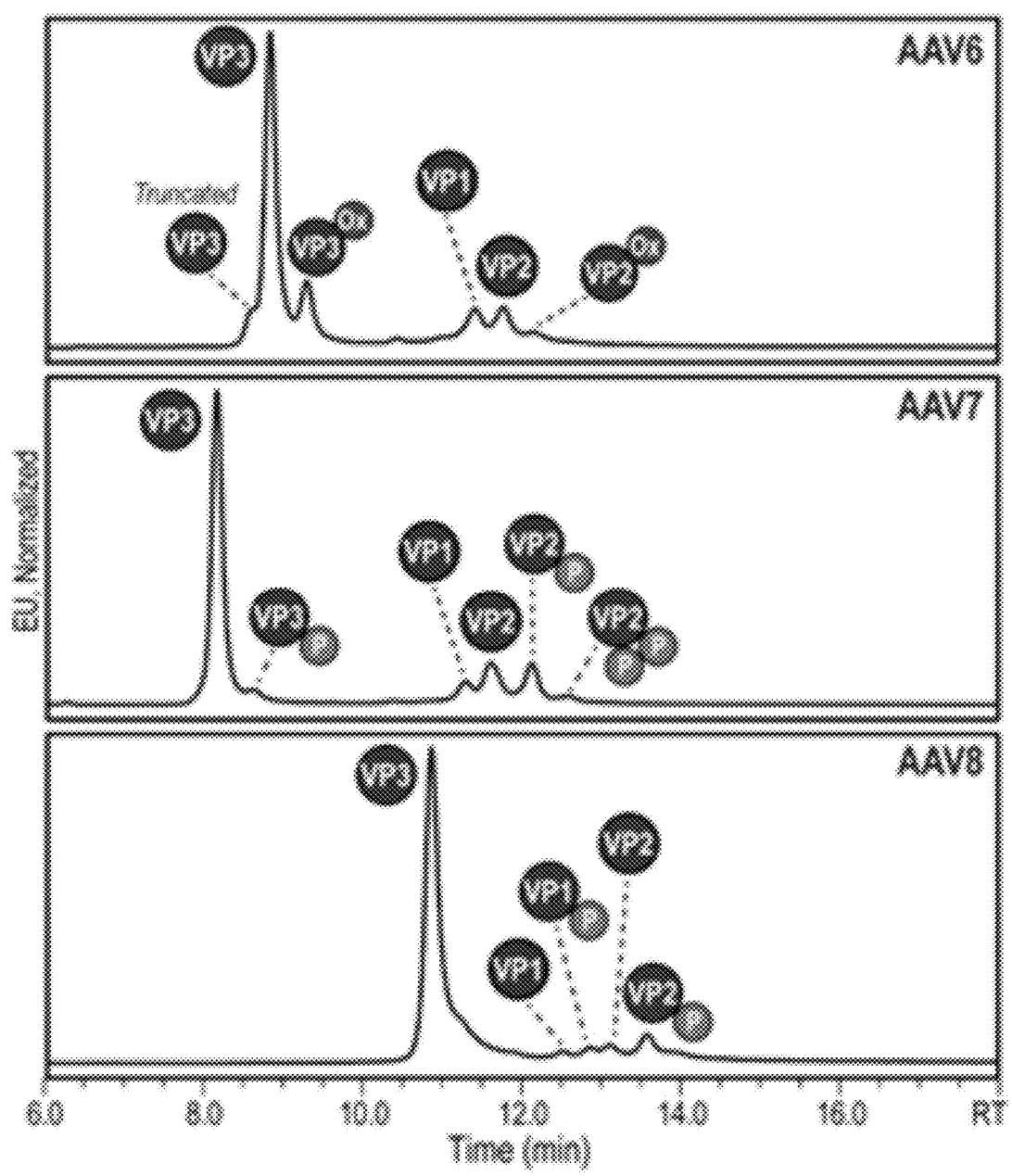
FIG. 7A shows comparison of fluorescent profiles of capsid viral proteins in AAV6, AAV7 and AAV8 samples using HILIC separation including a Waters ACQUITY UPLC Glycoprotein BEH Amide Column (300 Å, 1.7 2.1× 150 mm) according to an exemplary embodiment.

When three AAV serotypes (AAV6, AAV7, and AAV8) were separated using HILIC, the separation of three AAV serotypes resulted in several resolved or partially resolved peaks for each serotype, which were all subsequently identified by MS analysis. As shown in FIG. 7A, multiple peaks were observed corresponding to different capsid viral proteins, such as VP1, VP2, or VP3. The FLR traces were monitored using $\lambda_{em}$=280 nm and $\lambda_{ex}$=348 nm in FIG. 7A. FIG. 7A shows comparison of fluorescent profiles of capsid viral proteins in AAV6, AAV7 and AAV8 samples using HILIC separation including a Waters ACQUITY UPLC Glycoprotein BEH Amide Column (300 Å, 1.7 µm, 2.1×150 mm). These peaks also revealed variants of viral proteins including post-translation modifications. For HILIC analysis, the results indicated that VP3 was eluted prior to the elution of VP1 or VP2 as shown in FIG. 7A. VP1 contains the entire sequence of VP2. Since VP1 was eluted consistently prior to VP2 in HILIC column, the results implied that the unique N-terminus of VP1 may have relatively high hydrophobicity.

In addition, HILIC-FLR-MS analysis revealed several peaks that were attributed to oxidation and phosphorylation occurring on individual capsid viral proteins. The increased hydrophilicity due to the presence of certain post-translation modifications can change the retention time of the capsid proteins during the separations. The variant species of capsid viral proteins exhibited enhanced retention on the HILIC column and eluted slightly later than their unmodified counterparts. Furthermore, HILIC-FLR-MS analysis of AAV6 revealed a partially resolved small peak eluting slightly before the major VP3 as shown in FIG. 7A (top panel). This small peak was subsequently identified as an N-terminal fragment of VP3 which was derived from protein backbone clipping between Pro210 and Met211 with subsequent N-terminal Met loss and acetylation of the following alanine.

Figure 7B:
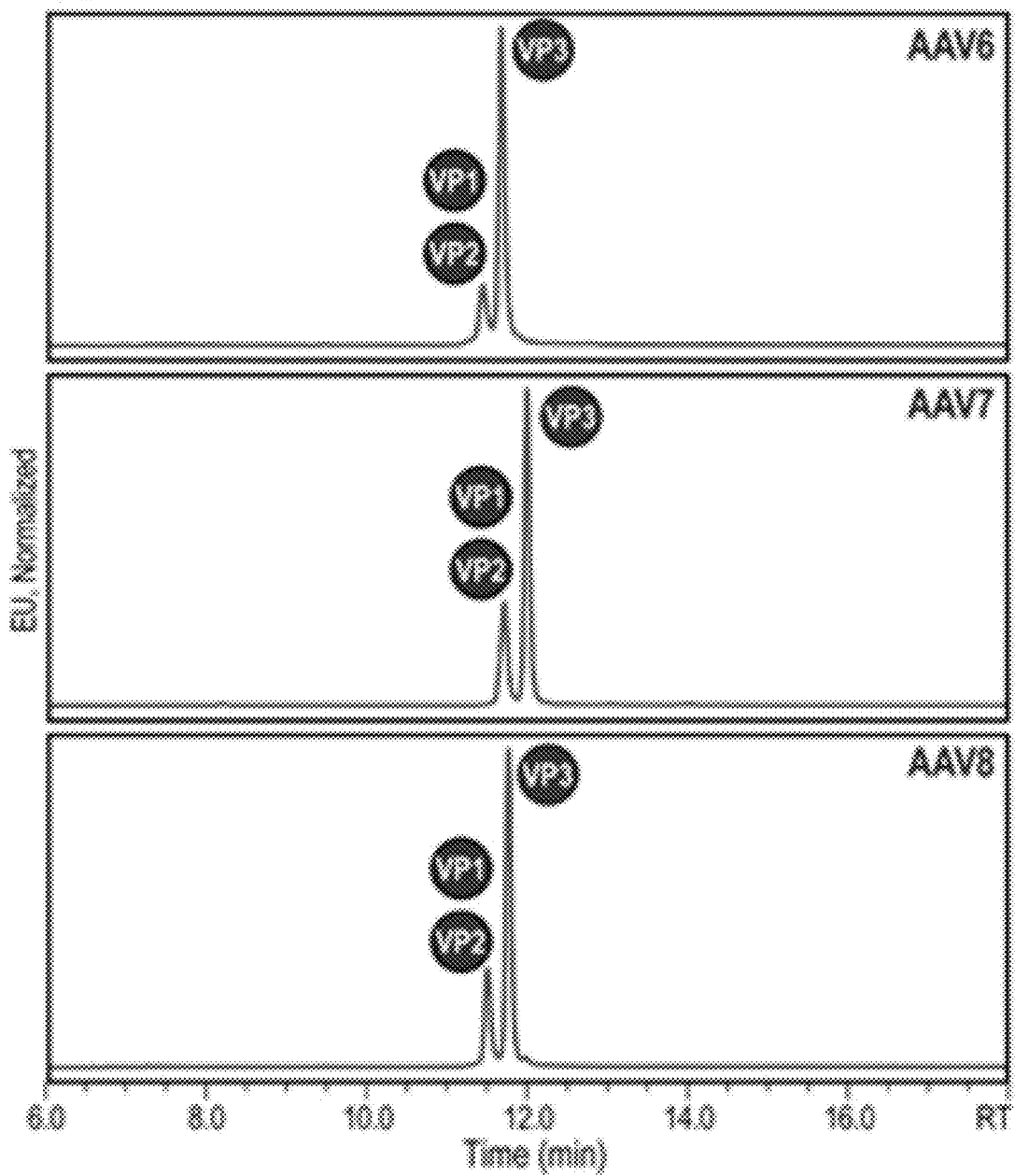
FIG. 7B shows comparison of fluorescent profiles of capsid viral proteins in AAV6, AAV7 and AAV8 samples using RPLC including a Waters ACQUITY UPLC Protein BEH C4 column (300 Å, 1.7 2.1×150 mm) according to an exemplary embodiment.

When three AAV serotypes (AAV6, AAV7, and AAV8) were separated using RPLC C4 column, only two chromatographic peaks were resolved, including the separation using extensive gradient optimization. Subsequent MS analysis confirmed the co-elution of VP1 and VP2 in first peak, followed by the elution of VP3 in second peak, as shown in FIG. 7B. The FLR traces were monitored using $\lambda_{em}$=280 nm and $\lambda_{ex}$=348 nm in FIG. 7B. FIG. 7B shows comparison of fluorescent profiles of capsid viral proteins in AAV6, AAV7 and AAV8 samples using RPLC including a Waters ACQUITY UPLC Protein BEH C4 column (300 Å, 1.7 µm, 2.1×150 mm). It is apparent that the HILIC method is superior than the RPLC method in separating AAV capsid proteins and their variant forms.

The post-translation modification of capsid proteins may affect the transduction efficiency of the AAV vector. It is important to monitor the oxidation and phosphorylation of capsid protein and any impact on the potency of AAV-based drug products from a process control perspective. A previous report has shown that tyrosine phosphorylation can negatively affect the transduction efficiency of the AAV2 vector (Zhong, L.; Li, B.; Jayandharan, G.; Mah, C. S.; Govindasamy, L.; Agbandje-McKenna, M.; Herzog, R. W.; Weigel-Van Aken, K. A.; Hobbs, J. A.; Zolotukhin, S.; Muzyczka, N.; Srivastava, A. *Virology* 2008, 381, 194-202). It shows that phosphorylation is a relevant quality attribute for AAV-based drug development.

Example 4

Strategies to Increase Sample Loading of HILIC Column

AAV samples are typically associated with low concentrations (0.01-0.1 mg/mL) (Rodrigues, G. A.; Shalaev, E.; Karami, T. K.; Cunningham, J.; Slater, N. K. H.; Rivers, H. M. *Pharmaceutical research* 2018, 36, 29). Concentrating AAV samples using centrifugal filtration can be troublesome, since significant sample losses can occur due to the adsorption of AAV on the membrane (Xie, Q.; Hare, J.; Turnigan, J.; Chapman, M. S. *J Virol Methods* 2004, 122, 17-27). It is preferable to analyze AAV samples directly in their stock solutions to eliminate artifact formation and poor sample recoveries from the pretreatment steps. One of the strategies is to increase the sample amount/volume in column loading to improve downstream detection. However, HILIC analysis has limitation on injection volume of aqueous samples, since HILIC separation is very sensitive to the mismatch between the sample solvent (water) and the mobile phase (high organic solvent). In the present application, the injection volume of AAV samples in HILIC analysis was kept at 1 µL to ensure optimal chromatographic performance. In order to increase the column loading greater than 1 µL without compromising the LC performance, two strategies were applied. One loading strategy was adjusting a larger aliquot of AAV stock solution (e.g. greater than 1 µL) with organic solvent to match the initial mobile phase conditions, and then injected in its entirety onto the HILIC column. This strategy was tested on a case-by-case basis, as many AAV samples could precipitate in high percentages of organic solvent. An alternative loading strategy was the use of multiple sample loading steps by repeating 1 µL injections of the AAV samples onto the HILIC column before initiating the gradient for AAV capsid protein elution and separation. Both strategies were used with greater flexibility to analyze diluted AAV samples directly without using pre-concentration.

Example 5

Increase Sensitivity of HILIC-MS Using Modified Desolvation Gas

The protein concentrations of the tested AAV samples were found to range from 0.01 to 0.09 µg/µL in the present application. For highly diluted AAV samples, up to 3 µL of the stock solution was injected onto the HILIC column using the aforementioned loading strategies, leading to a column loading amount of as little as about 30 ng. Although 30 ng AAV sample was sufficient for FLR detection due to the presence of multiple tryptophan residues in three capsid viral proteins from all serotypes, the low quantity of AAV samples still presented a significant challenge for MS analysis, particularly for detecting minor variant forms. This challenge was further compounded by the use of TFA as an ion-pairing reagent in the HILIC method due to ion suppression (Camperi, J.; Pichon, V.; Delaunay, N. *Journal of*

*pharmaceutical and biomedical analysis* 2020, 178, 112921). Previous studies provided a capillary HILIC-MS method by applying a dopant gas (ACN+1% propionic acid) to a Bruker CaptiveSpray ESI interface to reduce TFA ion suppression (Gargano, A. F. G.; Roca, L. S.; Fellers, R. T.; Bocxe, M.; Dominguez-Vega, E.; Somsen, G. W. *Analytical chemistry* 2018, 90, 6601-6609) in order to mitigate TFA-induced MS sensitivity loss. Previous studies also provided a device that could modify the desolvation gas on a Q-Exactive MS system for regular flow LC-MS analysis (Wang, S et al.).

Figure 8A:
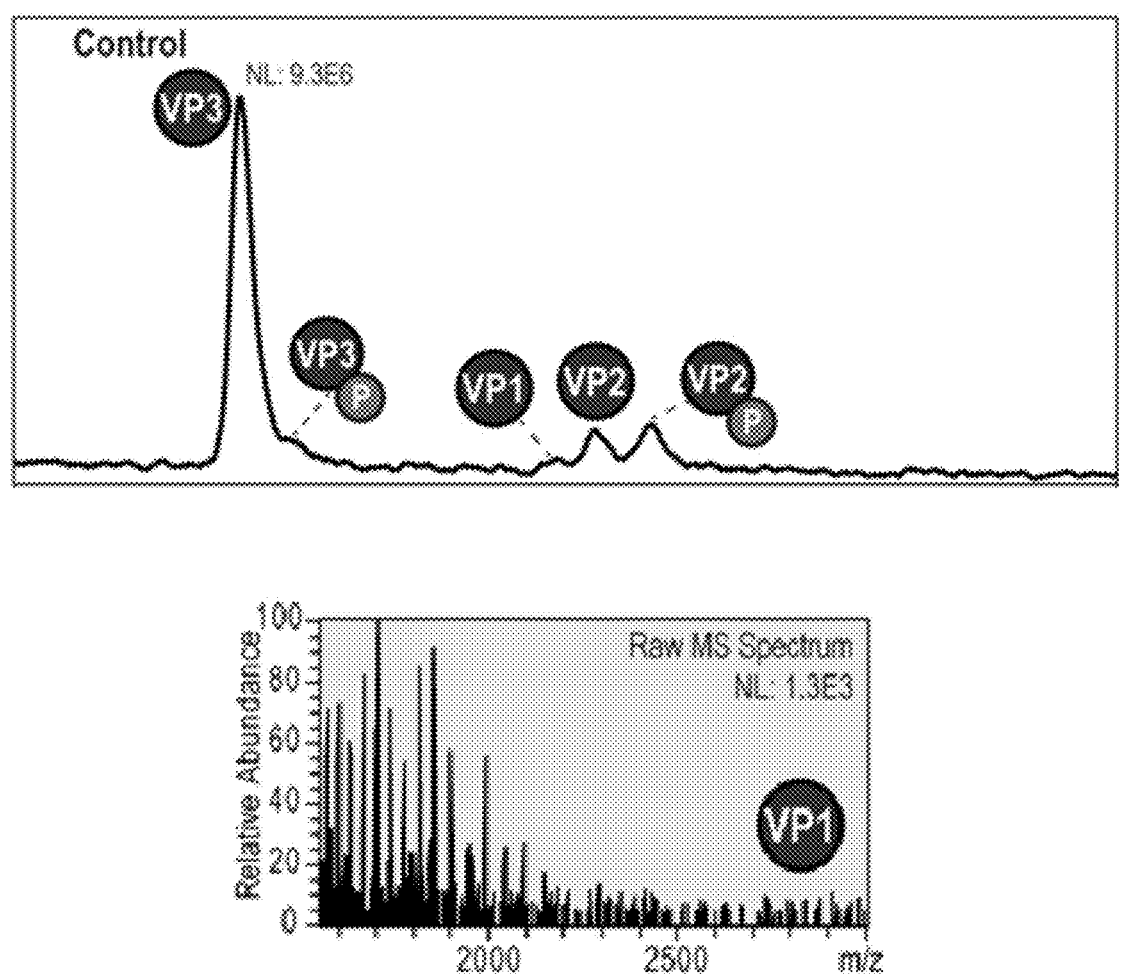
FIG. 8A shows total ion chromatograms (TICs) of HILIC-FLR-MS analysis of AAV7 without applying any desolvation gas according to an exemplary embodiment.

The present application provides a method by modifying the desolvation gas with acid vapor from a mixture of propionic acid (PA) and isopropanol (IPA) (3:1, v/v), and the results indicated that the MS responses of tryptic peptides from a TFA-based LC-MS analysis were increased by approximately five fold. The present application provided a desolvation gas modification device to improve the sensitivity of MS analysis. In order to improve the characterization of AAV capsid proteins, HILIC-FLR-MS analysis of an AAV7 sample was performed both with and without the use of PA/IPA modified desolvation gas, as shown in FIGS. 8A and 8B. By comparing the total ion chromatograms (TICs) and the raw MS spectra, the application of PA/IPA modified desolvation gas led to a significant improvement in MS sensitivity (about 2-3 folds) and spectrum quality. Compared to peptides, the gain in MS sensitivity by TFA-fix strategy is less prominent for capsid proteins, presumably due to a larger number of TFA anions residing on the protein surface that cannot be effectively replaced by PA during the ESI (Apffel, A.; Fischer, S.; Goldberg, G.; Goodley, P. C.; Kuhlmann, F. E. *J Chromatogr A* 1995, 712, 177-190). However, the apparent improvement in MS sensitivity, as achieved by the method of the present application, is still beneficial for the identification of those low-abundance proteoforms, such as VP1, which was expressed at much lower levels.

To counteract TFA-induced ion suppression, a desolvation gas modification device, delivering a dopant gas containing a 3:1 (v/v) ratio of propionic acid (PA) and isopropanol (IPA), was implemented on the ion source. FIG. 8A shows TICs of HILIC-FLR-MS analysis of AAV7 without applying any desolvation gas. FIG. 8B shows TICs of HILIC-FLR-MS analysis of AAV7 with desolvation gas (3:1 (v/v) mixture of propionic acid (PA) and isopropanol (IPA)). FIGS. 8A and 8B also show raw mass spectrum of VP1 from each sample.

Example 6

Using HILIC-FLR-MS to Analyze a Variety of AAV Serotypes

Figure 9A:
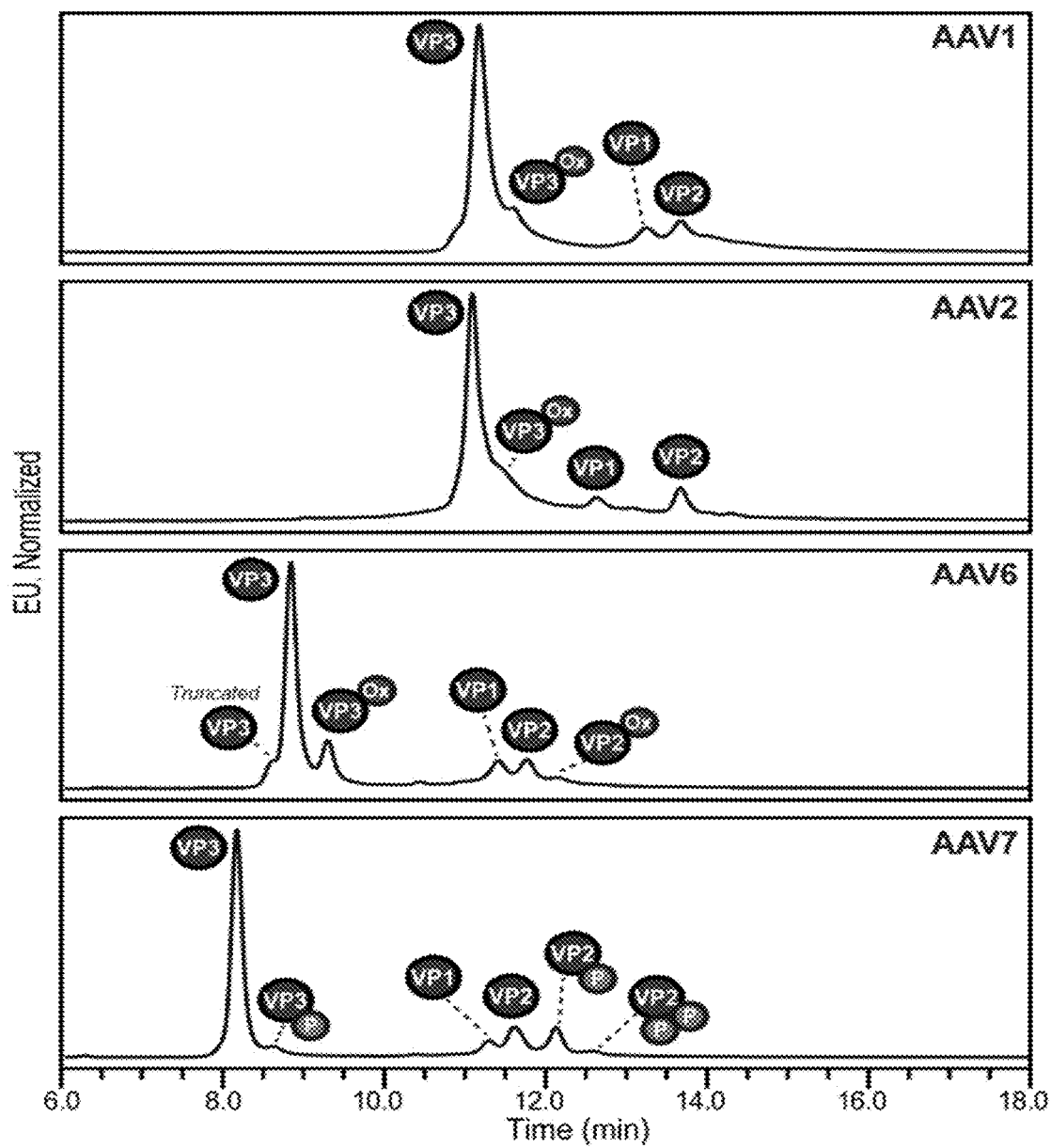
FIG. 9A shows the analysis of AAV1, AAV2, AAV6, and AAV7 serotypes using HILIC-FLR and monitored using $\lambda_{em}$=280 nm and $\lambda_{ex}$=348 nm according to an exemplary embodiment. The fluorescence intensity (EU) was normalized across all samples. The capsid protein identities of VP1, VP2, and VP3 of each AAV serotype and their oxidized (Ox) and phosphorylated variants (P) were identified according to an exemplary embodiment.
Figure 9B:
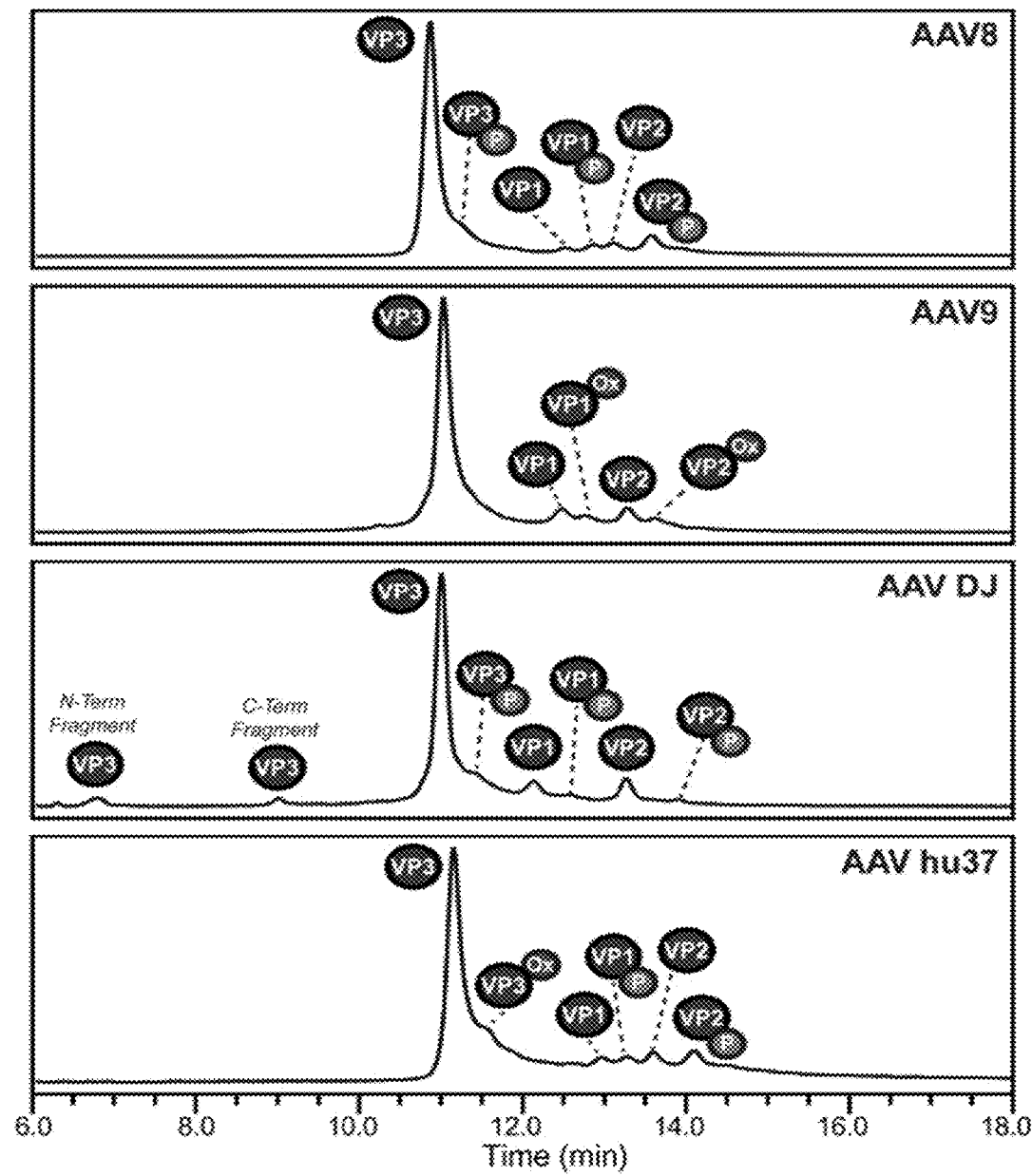
FIG. 9B shows the analysis of AAV8, AAV9, AAV DJ, and AAV hu37 serotypes using HILIC-FLR and monitored using $\lambda_{em}$=280 nm and $\lambda_{ex}$=348 nm according to an exemplary embodiment. The fluorescence intensity (EU) was normalized across all samples. The capsid protein identities of VP1, VP2, and VP3 of each AAV serotype and their oxidized (Ox) and phosphorylated variants (P) were identified according to an exemplary embodiment.

A variety of AAV serotypes (AAV1, AAV2, AAV6, AAV7, AAV8, AAV9, AAVDJ, and AAVhu37) were subjected to HILIC-FLR-MS analysis to characterize capsid proteins. Three capsid viral proteins, for example, VP1, VP2 and VP3, and their variant forms from each of the eight AAV serotypes were readily separated as shown in FIGS. 9A and 9B. The subsequent MS analysis, enhanced by PA/IPA modified desolvation gas, allowed sensitive and accurate mass measurement of each FLR peak, including the viral proteins which were present at low levels. As shown in FIGS. 9A and 9B, various AAV serotypes (AAV1, AAV2, AAV6, AAV7, AAV8, AAV9, AAV DJ, and AAV hu37) were analyzed using HILIC-FLR and monitored using $\lambda_{em}$=280 nm and $\lambda_{ex}$=348 nm. The fluorescence intensity (EU) was normalized across all samples. The capsid protein identities of VP1, VP2, and VP3 of each AAV serotype and their oxidized (Ox) and phosphorylated variants (P) were identified as shown in FIGS. 9A and 9B.

The identity of each AAV serotype was unambiguously confirmed based on three of its unique capsid proteins by comparing the observed and predicted masses with mass errors under 2 Da. In addition, the capsid protein variants were confidently identified with mass errors under 4 Da as a result of PTM formation or protein backbone clipping. The results of MS analysis confirmed the removal of the N-terminal methionine and the subsequent acetylation of the following alanine in VP1 and VP3, as well as the removal of the N-terminal threonine in VP2 from all serotypes.

Oxidized and phosphorylated variants were also identified in a majority of the tested AAV serotype samples. These variants exhibited enhanced retention on the HILIC column due to increased hydrophilicity and were effectively separated from the unmodified capsid proteins. The chromatographic separation step of HILIC-FLR significantly improved the MS detection of these low-abundance variants by reducing ion suppression from the co-eluting species and allowed accurate mass measurement of variants having small mass changes. Without chromatographic separation, low levels of oxidation variant (+16 Da) are unlikely to be detected by MS at intact capsid protein levels (60-80 kDa), as it is challenging to resolve its mass from that of the main species. In addition, the HILIC method is capable of separating capsid protein fragments. Analysis of AAVDJ revealed two low-abundance, early-eluting FLR peaks, which were identified as the N-terminal and C-terminal fragments of VP3, due to protein backbone clipping between Gly454 and Gly455 or Asn458 and Thr459, respectively.

The HILIC method is useful for capsid protein stoichiometry analysis due to good chromatographic resolution. By combining the FLR peaks of all proteoforms from each VP, an estimated stoichiometric ratio was calculated for each AAV serotype sample. A majority of AAV serotype samples exhibited ratios close to the expected value of 1:1:10 (VP1: VP2: VP3). However, a few samples showed ratios deviated from the expected value significantly. The HILIC method of the present application can be applied semi-quantitatively to compare the relative expression levels of the three VPs from different lots or processes.

Example 7

Using HILIC-FLR-MS for Batch-to-Batch Comparison

Figure 10:
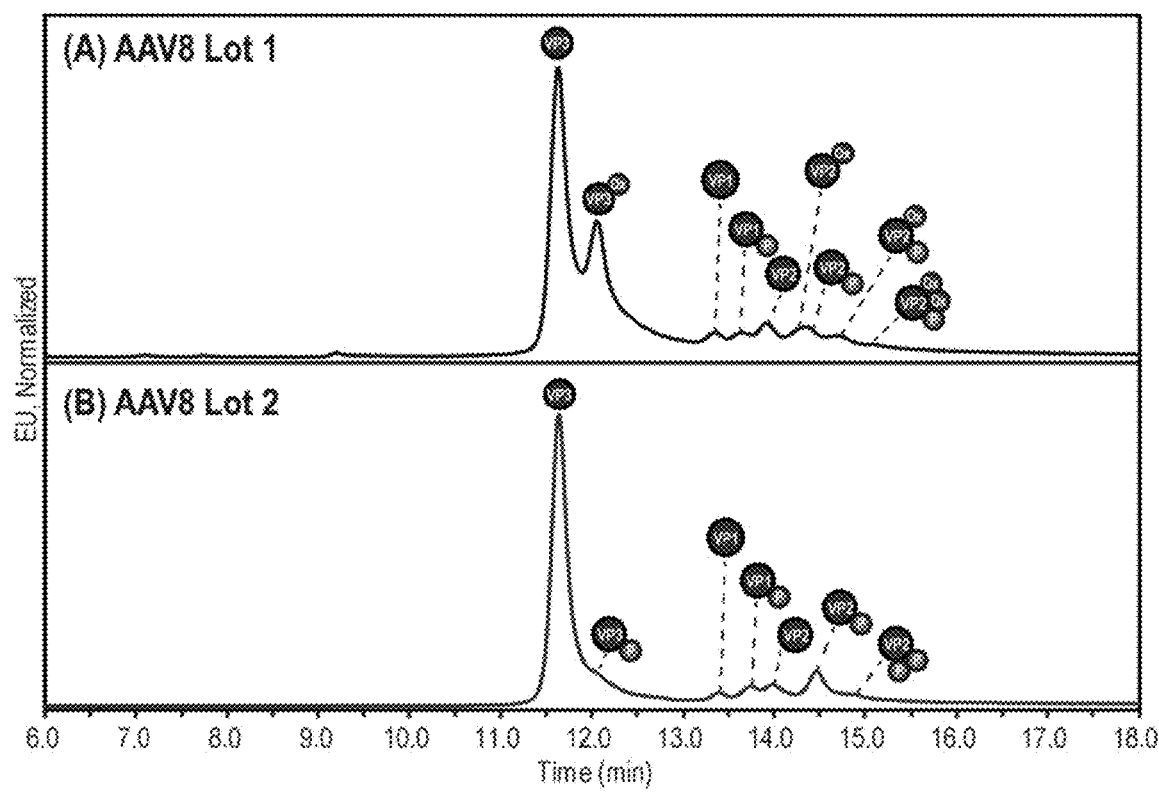
FIG. 10 shows the comparison of HILIC-FLR profiles of AAV8 Lot 1 and Lot 2 at capsid protein levels according to an exemplary embodiment. The capsid protein identities of VP1, VP2, and VP3 of each AAV serotype and their oxidized (Ox) and phosphorylated variants (P) were identified according to an exemplary embodiment.
Figure 11A:
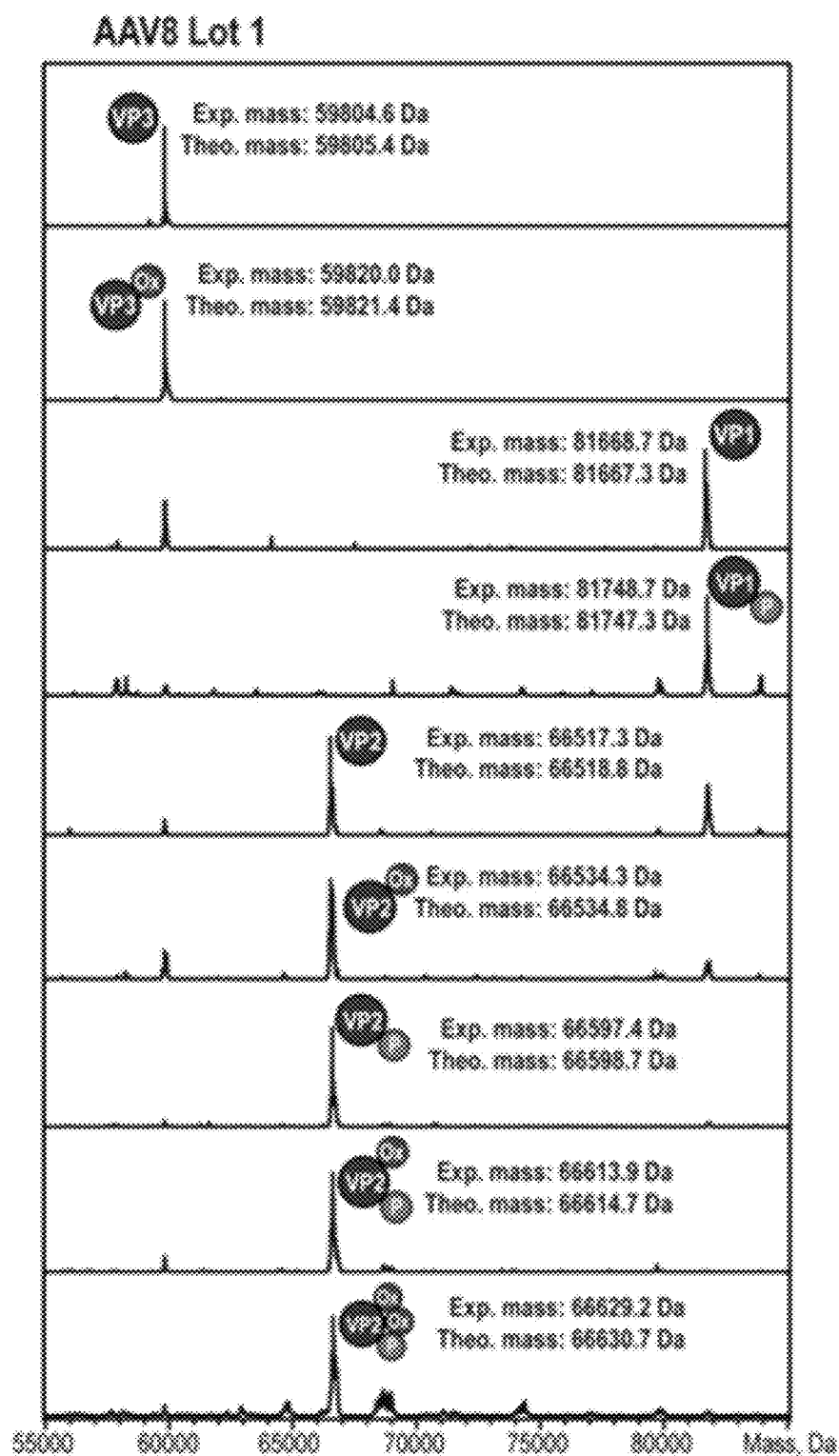
FIG. 11A shows deconvoluted mass spectrum of AAV8 peaks from AAV8 Lot 1 presented in elution order according to an exemplary embodiment. The capsid protein identities of VP1, VP2, and VP3 of each AAV serotype and their oxidized (Ox) and phosphorylated variants (P) were identified according to an exemplary embodiment.
Figure 11B:
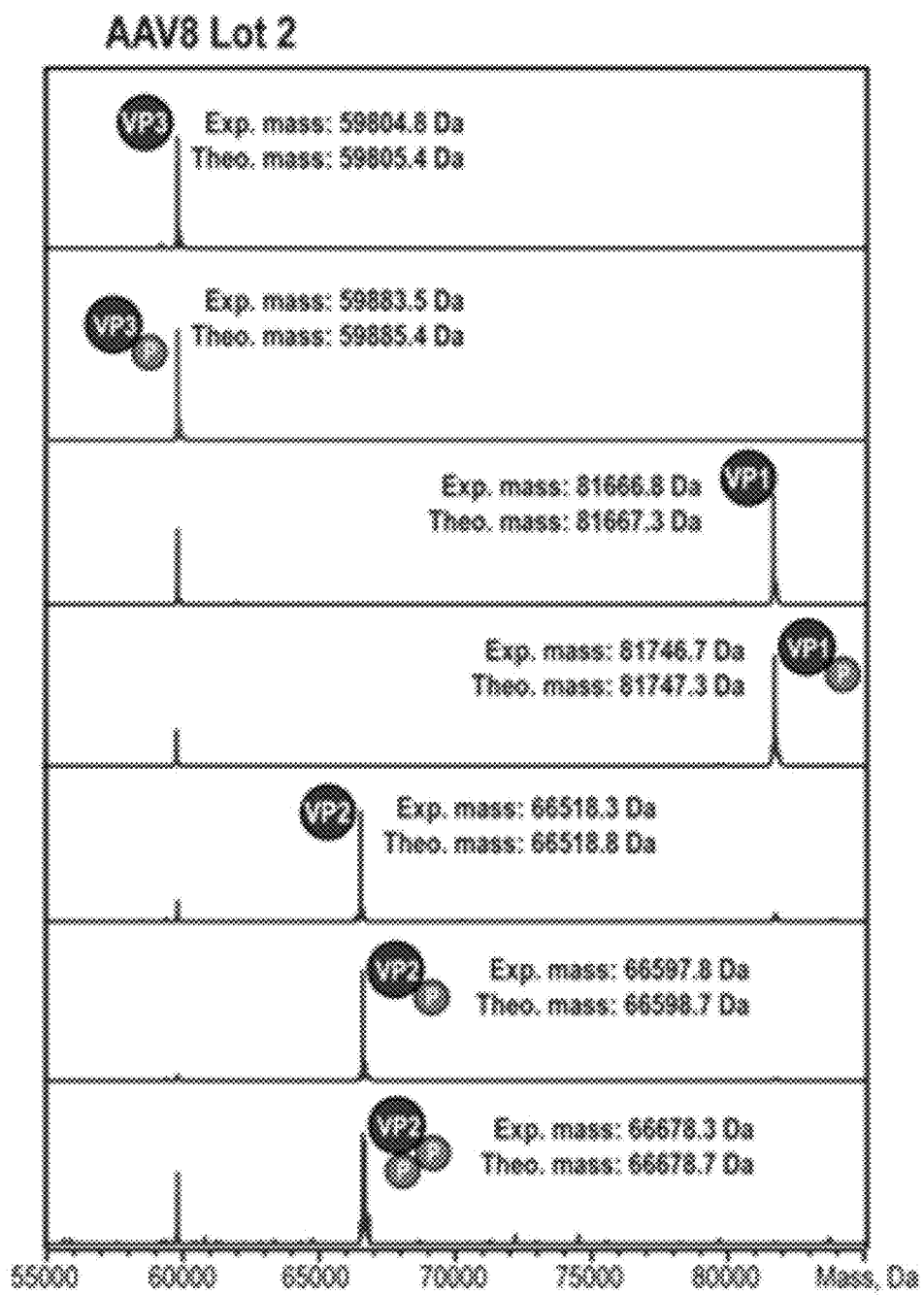
FIG. 11B shows deconvoluted mass spectrum of AAV8 peaks from AAV8 Lot 2 presented in elution order according to an exemplary embodiment. The capsid protein identities of VP1, VP2, and VP3 of each AAV serotype and their oxidized (Ox) and phosphorylated variants (P) were identified according to an exemplary embodiment.

Two AAV8 lots produced from two different processes were compared at capsid protein levels using the HILIC-FLR-MS method of the present application. The FLR profiles of AAV8 Lot 1 and Lot 2 were compared and monitored using $\lambda_{em}$=280 nm and $\lambda_{ex}$=348 nm. The fluorescence intensity (EU) was normalized across both samples as shown in FIG. 10. The capsid protein identities of VP1, VP2, and VP3 of each AAV serotype and their oxidized (Ox) and phosphorylated variants (P) were identified. The main FLR peaks (VP3) from two lots showed identical retention time. The overall FLR profiles showed notable differences as shown in FIG. 10. The mass spectrum of each FLR peak was averaged and deconvoluted, and the resulting spectra were shown in FIGS. 11A and 11B presented in elution order. The capsid protein identities of VP1, VP2, and VP3 of each AAV serotype and their oxidized (Ox) and phosphorylated variants (P) were identified. The identity of each FLR peak was assigned by comparing the observed and predicted masses in considering the presence of common PTMs. Each FLR peak was annotated. The results indicated that AAV8 Lot 1 exhibited higher levels of oxidation compared to AAV8 Lot 2. AAV8 Lot 2 showed significantly higher levels of phosphorylation compared to AAV8 Lot 1. Since both oxidation and phosphorylation can increase the hydrophilicity of the capsid viral proteins, the variants were eluted later than their unmodified forms on the HILIC column. VP2 with one oxidation and VP2 with two phosphorylations were both observed in Lot 1, their relative retention times indicated that phosphorylation had a slightly greater effect on increasing HILIC retention compared to oxidation.

Since the HILIC-FLR-MS method of the present application can enhance the sensitivity of MS analysis, low-abundance variants which were unique in each lot were confidently identified. VP2 with one oxidation and one phosphorylation was only observed in Lot 1. VP2 with two phosphorylation was only observed in Lot 2, which suggested the presence of two phosphorylation sites in VP2. Combining the results obtained from both lots, a total of 11 different proteoforms from the three capsid viral proteins were identified with mass errors all under 2 Da. The analysis results did not reveal any N-glycosylated capsid proteins. The results indicated that N-glycosylation may not presence or may presence at very low levels in these two AAV8 lots.

Peptide mapping analysis after tryptic digestion was conducted. The results confirmed all the findings of PTMs. The results indicated that higher levels of oxidation were found on several methionine residues (Met212, Met374, Met473 and Met561) in Lot 1 and a higher level of phosphorylation was found on Ser149 in Lot 2. N-glycosylated peptides were not detected in either lot. The results supported that the HILIC-FLR-MS method of the present application prevails in higher throughput and reduced sample processing, which is particularly valuable in supporting process development for evaluating a large number of samples a timely fashion. In addition, different proteoforms from each VP were combined, the capsid protein stoichiometry of each lot was estimated. The results indicated comparable capsid protein stoichiometry between two lots.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method of determining heterogeneity of protein components of a viral capsid of an intact, non-enveloped viral particle comprising: subjecting a sample comprising said viral particle to hydrophilic interaction liquid chromatography (HILIC) to separate protein components of the viral capsid of said viral particle; determining masses of said protein components of said viral capsid; comparing said determined masses of said protein components of said viral capsid with theoretical masses, wherein a deviation of one or more of said determined masses of said protein components of said viral capsid from the theoretical masses is indicative of a capsid heterogeneity.

2. The method of claim 1, wherein said heterogeneity comprises one or more of mixed serotypes, variant capsids, capsid protein amino acid substitutions, truncated capsid proteins, or modified capsid proteins.

3. A method for characterizing protein components of a viral capsid of an intact, non-enveloped viral particle, comprising: subjecting a sample comprising said viral particle to hydrophilic interaction liquid chromatography (HILIC) to separate protein components of said viral capsid of said viral particle, wherein said protein components are monitored using a fluorescence detector; and determining masses of said protein components of said viral capsid to identify said protein components separated by said HILIC.

4. The method of claim 3, wherein a mobile phase of said HILIC comprises trifluoroacetic acid, and wherein a desolvation gas is used in the separation of said protein components.

5. The method of claim 4, wherein said desolvation gas is modified by a dopant comprising propionic acid and isopropanol.

6. The method of claim 5, wherein a ratio of said propionic acid and said isopropanol is 3:1.

7. The method of claim 3, wherein said sample of said viral particle is mixed with a liquid prior to loading to said HILIC, wherein said liquid comprises one or more components of a mobile phase of said HILIC.

8. The method of claim 3, wherein said sample of said viral particle is loaded to said HILIC by multiple injections.

9. The method of claim 3, wherein said HILIC includes a wide-pore amide-bonded column.

10. The method of claim 3 further comprising determining a relative abundance of said protein components based on said HILIC separation, thereby determining a stoichiometry of said protein components of said viral capsid of said viral particle.

11. The method of claim 3 further comprising comparing said determined masses of said protein components of said viral capsid with theoretical masses, wherein a deviation of one or more of said determined masses of said protein components from said theoretical masses is indicative of a capsid heterogeneity.

12. The method of claim 11, wherein said capsid heterogeneity comprises one or more of mixed serotypes, variant capsids, capsid protein amino acid substitutions, truncated capsid proteins, or modified capsid proteins.

13. The method of claim 11, wherein said capsid heterogeneity is phosphorylation, oxidation or protein backbone clippings of said protein component.

14. The method of claim 2, wherein said protein component is VP1, VP2 or VP3 of an adeno-associated virus (AAV) particle.

15. The method of claim 3, wherein said viral particle comprises an AAV particle.

16. The method of claim 15, wherein a serotype of said AAV particle is AAV1, AAV2, AAV6, AAV7, AAV8, AAV9, AAVDJ, AAVhu37, or a variant thereof.

17. The method of claim 15, wherein said AAV particle comprises an AAV vector encoding a heterologous transgene or a recombinant AAV.

18. The method of claim 3, wherein said viral particle comprises a viral vector encoding a heterologous transgene or belongs to a viral family selected from the group consisting of Adenoviridae, Parvoviridae, Retroviridae, Baculoviridae, and Herpesviridae.

19. The method of claim 18, wherein said viral particle belongs to a viral genus selected from the group consisting of Atadenovirus, Aviadenovirus, Ichtadenovirus, Mastadenovirus, Siadenovirus, Ambidensovirus, Brevidensovirus, Hepandensovirus, Iteradensovirus, Penstyldensovirus, Amdoparvovirus, Aveparvovirus, Bocaparvovirus, Copiparvovirus, Dependoparvovirus, Erythroparvovirus, Protoparvovirus, Tetraparvovirus, Alpharetrovirus, Betaretrovirus, Deltaretrovirus, Epsilonretrovirus, Gammaretrovirus, Lentivirus, Spumavirus, Alphabaculovirus, Betabaculovirus, Deltabaculovirus, Gammabaculovirus, Iltovirus, Mardivirus, Simplexvirus, Varicellovirus, Cytomegalovirus, Muromegalovirus, Proboscivirus, Roseolovirus, Lymphocryptovirus, Macavirus, Percavirus, and Rhadinovirus.

20. The method of claim 18, wherein said Retroviridae is Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend virus, Murine Stem Cell Virus (MSCV) Rous Sarcoma Virus (RSV), human T cell leukemia viruses, Human Immunodeficiency Viruse (HIV), feline immunodeficiency virus (Hy), equine immunodeficiency virus (Hy), visna-maedi virus; caprine arthritis-encephalitis virus; equine infectious anemia virus; feline immunodeficiency virus (Hy); bovine immune deficiency virus (BIV); or simian immunodeficiency virus (SIV).

21. The method of claim 3, wherein said HILIC uses a mobile phase A comprising trifluoroacetic acid in water or a mobile phase B comprising trifluoroacetic acid in acetonitrile.

22. The method of claim 21, wherein said mobile phase A or said mobile phase B comprises about 0.1% v/v trifluoroacetic acid.

* * * * *